United States Patent
Kobayashi et al.

(10) Patent No.: US 9,127,054 B2
(45) Date of Patent: Sep. 8, 2015

(54) IMMUNOASSAY OF COFILIN 1 PROTEIN

(75) Inventors: Michimoto Kobayashi, Kamakura (JP); Yoshinori Tanaka, Kamakura (JP); Aiko Takayama, Kamakura (JP); Satoko Kanamori, Kamakura (JP); Giman Jung, Kamakura (JP); Yoshiharu Sakai, Kyoto (JP); Hiroshi Okabe, Kyoto (JP)

(73) Assignees: TORAY INDUSTRIES, INC., Tokyo (JP); KYOTO UNIVERSITY, Kyoto-Shi (JP)

( * ) Notice: Subject to any disclaimer, the term of this patent is extended or adjusted under 35 U.S.C. 154(b) by 74 days.

(21) Appl. No.: 13/992,567

(22) PCT Filed: Dec. 5, 2011

(86) PCT No.: PCT/JP2011/078091
§ 371 (c)(1),
(2), (4) Date: Jun. 7, 2013

(87) PCT Pub. No.: WO2012/077643
PCT Pub. Date: Jun. 14, 2012

(65) Prior Publication Data
US 2013/0288277 A1    Oct. 31, 2013

(30) Foreign Application Priority Data
Dec. 9, 2010 (JP) .................. 2010-274879

(51) Int. Cl.
C07K 16/18     (2006.01)
G01N 33/577    (2006.01)
G01N 33/574    (2006.01)

(52) U.S. Cl.
CPC .............. *C07K 16/18* (2013.01); *G01N 33/577* (2013.01); *G01N 33/57446* (2013.01); *C07K 2317/34* (2013.01)

(58) Field of Classification Search
CPC .............. C07K 16/00–16/468; C07K 2317/34; G01N 33/577; G01N 33/57746
See application file for complete search history.

(56) References Cited

U.S. PATENT DOCUMENTS

| 6,162,902 A | 12/2000 | Mischak et al. |
| 2006/0029956 A1 | 2/2006 | Beyer et al. |
| 2009/0092596 A1 | 4/2009 | Haley et al. |
| 2010/0183604 A1 | 7/2010 | Ohta et al. |
| 2013/0011865 A1* | 1/2013 | Kobayashi et al. ......... 435/7.92 |

FOREIGN PATENT DOCUMENTS

| CN | 1931373 A | 3/2007 |
| CN | 101389962 A | 3/2009 |
| JP | 2000-507094 A | 6/2000 |
| JP | 2007-290984 A | 11/2007 |
| JP | 2008-506123 A | 2/2008 |
| WO | WO 2008/112424 A1 | 9/2008 |
| WO | WO 2008/156153 A1 | 12/2008 |
| WO | WO 2009/009890 A1 | 1/2009 |
| WO | WO 2009/045389 A2 | 4/2009 |

OTHER PUBLICATIONS

Myhrinder et al., Blood 2008; 111:3838-48.*
Bussone et al., Arthritis Res. Therapy 2011; 13:R74, pp. 1-13.*
BLAST alignment UniProt Entry P23528 human Cofilin, prepared Nov. 10, 2014.*
Shaw et al., Electrophoresis 2004; 25:2611-20.*
Chen et al., "Analysis of HK-2 cells exposed to oxalate and calcium oxalate crystals: proteomic insights into the molecular mechanisms of renal injury and stoe formation," Urological Research, vol. 38, 2010 (Published online Oct. 28, 2009), pp. 7-15.
Abe, H. et al., "A Cofilin-Like Protein is Involved in the Regulation of Actin Assembly in Developing Skeletal Muscle," Journal of Biochemistry, vol. 106, 1989, pp. 696-702.
Amano, Y. et al., "Jido Kagaku Hakko Koso Men'eki Bunseki Sochi 'SphereLight180' ni yoru ProGRP Sokutei no Kiso Kento," Abstracts of the 34th Annual Meeting of the Japan Society for Clinical Laboratory Automation, Aug. 1, 2002, p. 549.
Chan, A.Y. et al., "Role of Cofilin in Epidermal Growth Factor—Stimulated Actin Polymerization and Lamellipod Protrusion," Journal of Cell Biology, vol. 148, No. 3, Feb. 7, 2000, pp. 531-542.
Fujirebio Inc., "C-Peptide Kit, Lumipulse C-Peptide," Oct. 2007.
International search report issued in PCT/JP2011/078091 mailed Feb. 21, 2012.
Ogawa, K. et al., "Coding sequence of human placenta Cofilin cDNA," Nucleic Acids Research, vol. 18, No. 23, 1990, p. 7169.
Wang, K. et al., "Enhanced Invasive and Metastatic Potential Induced by Transforming Growth Factor-β1 Might be Correlated with Glutathione-S-transferase-π, Cofilin and Heat Shock Protein 27 in SGC-7901 Gastric Cancer Cells," Acta Biochimica et Biophysica Sinica, vol. 39, No. 7, 2007, pp. 520-526.
Wang, W. et al., "The activity status of cofilin is directly related to invasion, intravasation, and metastasis of mammary tumors," Journal of Cell Biology, vol. 173, No. 3, May 8, 2006, pp. 395-404.

(Continued)

*Primary Examiner* — Sheela J Huff
*Assistant Examiner* — Jessica H Roark
(74) *Attorney, Agent, or Firm* — Birch, Stewart, Kolasch & Birch, LLP

(57) ABSTRACT

An object of the present invention is to realize an antibody or a fragment thereof specifically recognizing a cofilin 1 protein, and a method for detecting and testing gastrointestinal cancer with high detection performance, which comprises performing immunoassay of the cofilin 1 protein using the antibody or a fragment thereof. An immunoassay of cofilin 1 protein is characterized by measuring cofilin 1 or a fragment thereof in a sample using 2 or more types of anti-cofilin 1 monoclonal antibody or fragments thereof specifically recognizing different peptide regions in the amino acid sequence constituting the cofilin 1 protein.

17 Claims, 6 Drawing Sheets

(56) References Cited

OTHER PUBLICATIONS

Yan, B. et al., "Cofilin immunolabelling correlates with depth of invasion in gastrointestinal endocrine cell tumors," Acta Histochemica, vol. 112, 2010, pp. 101-106.

Estornes et al., "Differential involvement of destrin and cofilin-1 in the control of invasive properties of Isreco1 human colon cancer cells", Int. J. Cancer: 121, pp. 2162-2171, 2007.

European Search Report dated Jun. 28, 2013 for Application No. 11750735.0.

Degen et al., "Tenascin-W, a new marker of cancer stroma, is elevated in sera of colon and breast cancer patients," International Journal of Cancer, vol. 122, pp. 2454-2461, 2008, XP002508351.

Extended European Search Report dated Aug. 20, 2014 for European Application No. 11846996.4.

UniProt, Cofilin-1, Printed Oct. 5, 2013.

\* cited by examiner

Fig. 4
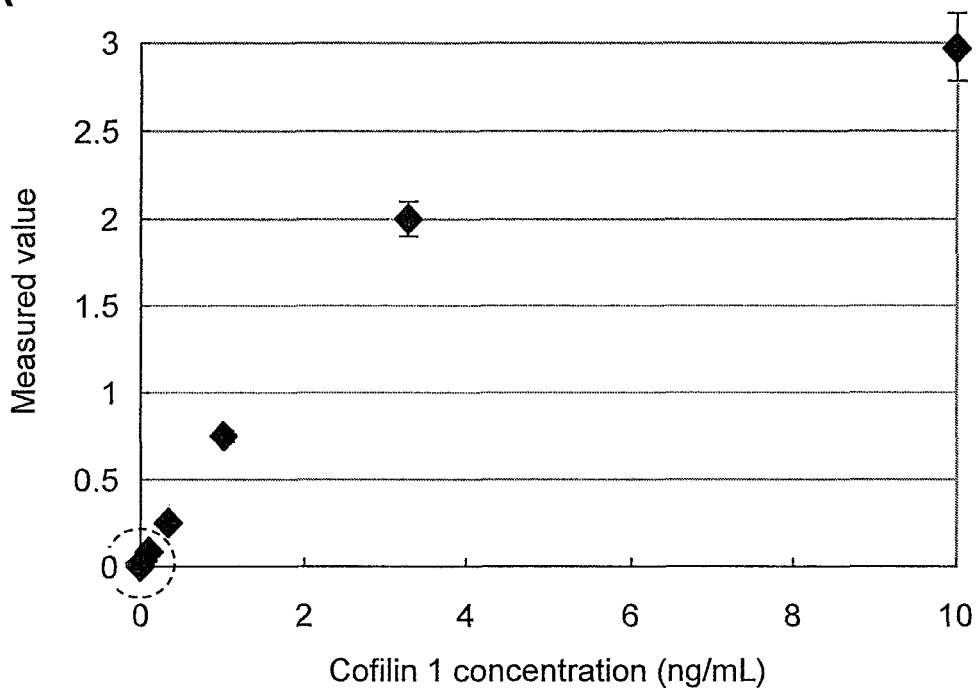
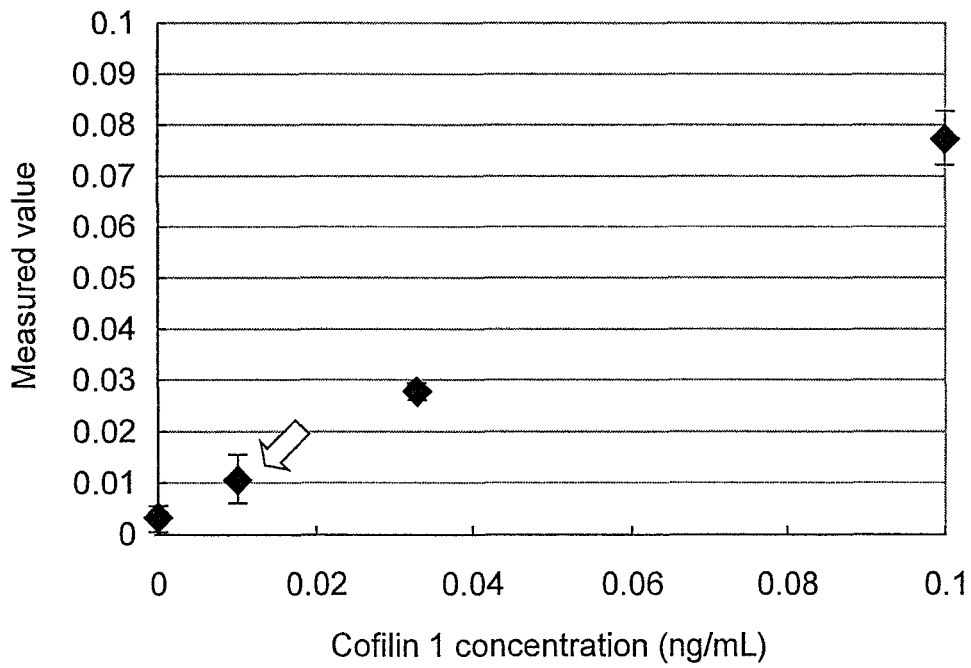

SEQUENCE LISTING

<160> NUMBER OF SEQ ID NOS: 40

<210> SEQ ID NO 1
<211> LENGTH: 45
<212> TYPE: PRT
<213> ORGANISM: Artificial
<220> FEATURE:
<223> OTHER INFORMATION: epitope sequence

```
<400> SEQUENCE: 1

Asp Ala Ile Lys Lys Leu Thr Gly Ile Lys His Glu Leu Gln Ala
1               5                  10                  15

Asn Cys Tyr Glu Glu Val Lys Asp Arg Cys Thr Leu Ala Glu Lys Leu
            20                  25                  30

Gly Gly Ser Ala Val Ile Ser Leu Glu Gly Lys Pro Leu
        35                  40                  45

<210> SEQ ID NO 2
<211> LENGTH: 54
<212> TYPE: PRT
<213> ORGANISM: Artificial
<220> FEATURE:
<223> OTHER INFORMATION: epitope sequence

<400> SEQUENCE: 2

Met Ala Ser Gly Val Ala Val Ser Asp Gly Val Ile Lys Val Phe Asn
1               5                  10                  15

Asp Met Lys Val Arg Lys Ser Ser Thr Pro Glu Glu Val Lys Lys Arg
            20                  25                  30

Lys Lys Ala Val Leu Phe Cys Leu Ser Glu Asp Lys Lys Asn Ile Ile
        35                  40                  45

Leu Glu Glu Gly Lys Glu
    50

<210> SEQ ID NO 3
<211> LENGTH: 40
<212> TYPE: PRT
<213> ORGANISM: Artificial
<220> FEATURE:
<223> OTHER INFORMATION: epitope sequence

<400> SEQUENCE: 3

Lys Leu Thr Gly Ile Lys His Glu Leu Gln Ala Asn Cys Tyr Glu Glu
1               5                  10                  15

Val Lys Asp Arg Cys Thr Leu Ala Glu Lys Leu Gly Gly Ser Ala Val
            20                  25                  30

Ile Ser Leu Glu Gly Lys Pro Leu
        35                  40

<210> SEQ ID NO 4
<211> LENGTH: 49
<212> TYPE: PRT
<213> ORGANISM: Artificial
<220> FEATURE:
<223> OTHER INFORMATION: epitope sequence

<400> SEQUENCE: 4

Met Ala Ser Gly Val Ala Val Ser Asp Gly Val Ile Lys Val Phe Asn
1               5                  10                  15

Asp Met Lys Val Arg Lys Ser Ser Thr Pro Glu Glu Val Lys Lys Arg
            20                  25                  30

Lys Lys Ala Val Leu Phe Cys Leu Ser Glu Asp Lys Lys Asn Ile Ile
        35                  40                  45

Leu

<210> SEQ ID NO 5
<211> LENGTH: 20
<212> TYPE: PRT
<213> ORGANISM: Artificial
<220> FEATURE:
```

```
<223> OTHER INFORMATION: epitope sequence

<400> SEQUENCE: 5

Lys Leu Thr Gly Ile Lys His Glu Leu Gln Ala Asn Cys Tyr Glu Glu
1               5                   10                  15

Val Lys Asp Arg
            20

<210> SEQ ID NO 6
<211> LENGTH: 9
<212> TYPE: PRT
<213> ORGANISM: Artificial
<220> FEATURE:
<223> OTHER INFORMATION: epitope sequence

<400> SEQUENCE: 6

Val Ile Ser Leu Glu Gly Lys Pro Leu
1               5

<210> SEQ ID NO 7
<211> LENGTH: 21
<212> TYPE: PRT
<213> ORGANISM: Artificial
<220> FEATURE:
<223> OTHER INFORMATION: epitope sequence

<400> SEQUENCE: 7

Val Lys Lys Arg Lys Lys Ala Val Leu Phe Cys Leu Ser Glu Asp Lys
1               5                   10                  15

Lys Asn Ile Ile Leu
            20

<210> SEQ ID NO 8
<211> LENGTH: 15
<212> TYPE: PRT
<213> ORGANISM: Artificial
<220> FEATURE:
<223> OTHER INFORMATION: antibody protein sequence

<400> SEQUENCE: 8

Lys Ala Ser Gln Ser Val Asp Tyr Asp Gly Asp Ser Tyr Val Asn
1               5                   10                  15

<210> SEQ ID NO 9
<211> LENGTH: 7
<212> TYPE: PRT
<213> ORGANISM: Artificial
<220> FEATURE:
<223> OTHER INFORMATION: antibody protein sequence

<400> SEQUENCE: 9

Ala Ala Ser Asn Leu Glu Ser
1               5

<210> SEQ ID NO 10
<211> LENGTH: 9
<212> TYPE: PRT
<213> ORGANISM: Artificial
<220> FEATURE:
<223> OTHER INFORMATION: antibody protein sequence

<400> SEQUENCE: 10

Gln Gln Ser Asn Glu Tyr Pro Trp Thr
1               5
```

```
<210> SEQ ID NO 11
<211> LENGTH: 5
<212> TYPE: PRT
<213> ORGANISM: Artificial
<220> FEATURE:
<223> OTHER INFORMATION: antibody protein sequence

<400> SEQUENCE: 11

Thr Tyr Pro Ile Glu
1               5

<210> SEQ ID NO 12
<211> LENGTH: 17
<212> TYPE: PRT
<213> ORGANISM: Artificial
<220> FEATURE:
<223> OTHER INFORMATION: antibody protein sequence

<400> SEQUENCE: 12

Tyr Phe His Pro Tyr Asn Asp Asp Thr Lys Tyr Asn Glu Lys Phe Lys
1               5                   10                  15

Gly

<210> SEQ ID NO 13
<211> LENGTH: 5
<212> TYPE: PRT
<213> ORGANISM: Artificial
<220> FEATURE:
<223> OTHER INFORMATION: antibody protein sequence

<400> SEQUENCE: 13

Gly Gly Phe Asp Tyr
1               5

<210> SEQ ID NO 14
<211> LENGTH: 15
<212> TYPE: PRT
<213> ORGANISM: Artificial
<220> FEATURE:
<223> OTHER INFORMATION: antibody protein sequence

<400> SEQUENCE: 14

Lys Ala Ser Gln Ser Val Asp Asp Asp Gly Asp Ser Tyr Met Asn
1               5                   10                  15

<210> SEQ ID NO 15
<211> LENGTH: 7
<212> TYPE: PRT
<213> ORGANISM: Artificial
<220> FEATURE:
<223> OTHER INFORMATION: antibody protein sequence

<400> SEQUENCE: 15

Ala Ala Ser Asn Leu Glu Ser
1               5

<210> SEQ ID NO 16
<211> LENGTH: 9
<212> TYPE: PRT
<213> ORGANISM: Artificial
<220> FEATURE:
<223> OTHER INFORMATION: antibody protein sequence

<400> SEQUENCE: 16

Gln Gln Ile Asn Glu Asp Pro Trp Thr
1               5
```

<210> SEQ ID NO 17
<211> LENGTH: 5
<212> TYPE: PRT
<213> ORGANISM: Artificial
<220> FEATURE:
<223> OTHER INFORMATION: antibody protein sequence

<400> SEQUENCE: 17

Thr Tyr Pro Ile Glu
1               5

<210> SEQ ID NO 18
<211> LENGTH: 17
<212> TYPE: PRT
<213> ORGANISM: Artificial
<220> FEATURE:
<223> OTHER INFORMATION: antibody protein sequence

<400> SEQUENCE: 18

Asn Phe His Pro Tyr Asn Asp Asp Thr Lys Tyr Asn Glu Lys Phe Lys
1               5                   10                  15

Gly

<210> SEQ ID NO 19
<211> LENGTH: 5
<212> TYPE: PRT
<213> ORGANISM: Artificial
<220> FEATURE:
<223> OTHER INFORMATION: antibody protein sequence

<400> SEQUENCE: 19

Gly Gly Phe Asp Tyr
1               5

<210> SEQ ID NO 20
<211> LENGTH: 15
<212> TYPE: PRT
<213> ORGANISM: Artificial
<220> FEATURE:
<223> OTHER INFORMATION: antibody protein sequence

<400> SEQUENCE: 20

Arg Ala Ser Lys Ser Val Thr Thr Ser Gly Tyr Ser Tyr Met His
1               5                   10                  15

<210> SEQ ID NO 21
<211> LENGTH: 7
<212> TYPE: PRT
<213> ORGANISM: Artificial
<220> FEATURE:
<223> OTHER INFORMATION: antibody protein sequence

<400> SEQUENCE: 21

Leu Ala Ser Asn Leu Glu Ser
1               5

<210> SEQ ID NO 22
<211> LENGTH: 9
<212> TYPE: PRT
<213> ORGANISM: Artificial
<220> FEATURE:
<223> OTHER INFORMATION: antibody protein sequence

<400> SEQUENCE: 22

Gln His Thr Arg Glu Leu Pro Tyr Thr
1               5

```
<210> SEQ ID NO 23
<211> LENGTH: 5
<212> TYPE: PRT
<213> ORGANISM: Artificial
<220> FEATURE:
<223> OTHER INFORMATION: antibody protein sequence

<400> SEQUENCE: 23

Ser Tyr Thr Met Ser
1               5

<210> SEQ ID NO 24
<211> LENGTH: 17
<212> TYPE: PRT
<213> ORGANISM: Artificial
<220> FEATURE:
<223> OTHER INFORMATION: antibody protein sequence

<400> SEQUENCE: 24

Thr Ile Ser Val Gly Gly Ser Tyr Thr Tyr Tyr Pro Asp Ser Val Lys
1               5                   10                  15

Gly

<210> SEQ ID NO 25
<211> LENGTH: 7
<212> TYPE: PRT
<213> ORGANISM: Artificial
<220> FEATURE:
<223> OTHER INFORMATION: antibody protein sequence

<400> SEQUENCE: 25

Arg Glu Gly Tyr Phe Asp Val
1               5

<210> SEQ ID NO 26
<211> LENGTH: 17
<212> TYPE: PRT
<213> ORGANISM: Artificial
<220> FEATURE:
<223> OTHER INFORMATION: antibody protein sequence

<400> SEQUENCE: 26

Lys Ser Ser Gln Ser Leu Leu Asn Ser Asn Asn Gln Lys Asn Tyr Leu
1               5                   10                  15

Ala

<210> SEQ ID NO 27
<211> LENGTH: 7
<212> TYPE: PRT
<213> ORGANISM: Artificial
<220> FEATURE:
<223> OTHER INFORMATION: antibody protein sequence

<400> SEQUENCE: 27

Phe Ala Ser Thr Arg Glu Ser
1               5

<210> SEQ ID NO 28
<211> LENGTH: 9
<212> TYPE: PRT
<213> ORGANISM: Artificial
<220> FEATURE:
<223> OTHER INFORMATION: antibody protein sequence

<400> SEQUENCE: 28
```

```
Gln Gln His Phe Ser Thr Pro Leu Thr
1               5
```

<210> SEQ ID NO 29
<211> LENGTH: 5
<212> TYPE: PRT
<213> ORGANISM: Artificial
<220> FEATURE:
<223> OTHER INFORMATION: antibody protein sequence

<400> SEQUENCE: 29

```
Tyr Tyr Tyr Met Ser
1               5
```

<210> SEQ ID NO 30
<211> LENGTH: 17
<212> TYPE: PRT
<213> ORGANISM: Artificial
<220> FEATURE:
<223> OTHER INFORMATION: antibody protein sequence

<400> SEQUENCE: 30

```
Val Ile Asn Ser Asn Gly Gly Asn Thr Tyr Tyr Ser Asp Thr Val Lys
1               5                   10                  15

Gly
```

<210> SEQ ID NO 31
<211> LENGTH: 16
<212> TYPE: PRT
<213> ORGANISM: Artificial
<220> FEATURE:
<223> OTHER INFORMATION: antibody protein sequence

<400> SEQUENCE: 31

```
His Gly Gly Tyr Gly Tyr Gly Tyr Ala Gly Tyr Trp Tyr Phe Asp Val
1               5                   10                  15
```

<210> SEQ ID NO 32
<211> LENGTH: 28
<212> TYPE: DNA
<213> ORGANISM: Artificial
<220> FEATURE:
<223> OTHER INFORMATION: Primer sequence

<400> SEQUENCE: 32
ctcggatcct tcgtttccgg aaacatgg                                      28

<210> SEQ ID NO 33
<211> LENGTH: 27
<212> TYPE: DNA
<213> ORGANISM: Artificial
<220> FEATURE:
<223> OTHER INFORMATION: Primer sequence

<400> SEQUENCE: 33
ccaggatccg tgaagaagcg caagaag                                       27

<210> SEQ ID NO 34
<211> LENGTH: 27
<212> TYPE: DNA
<213> ORGANISM: Artificial
<220> FEATURE:
<223> OTHER INFORMATION: Primer sequence

<400> SEQUENCE: 34
atcggatccg aggagggcaa ggagatc          27

<210> SEQ ID NO 35
<211> LENGTH: 27
<212> TYPE: DNA
<213> ORGANISM: Artificial
<220> FEATURE:
<223> OTHER INFORMATION: Primer sequence

<400> SEQUENCE: 35
ctggaattca actggggtga agggatt          27

<210> SEQ ID NO 36
<211> LENGTH: 29
<212> TYPE: DNA
<213> ORGANISM: Artificial
<220> FEATURE:
<223> OTHER INFORMATION: Primer sequence

<400> SEQUENCE: 36
gaggaattct aactgccccc cagcttctc        29

<210> SEQ ID NO 37
<211> LENGTH: 27
<212> TYPE: DNA
<213> ORGANISM: Artificial
<220> FEATURE:
<223> OTHER INFORMATION: Primer sequence

<400> SEQUENCE: 37
ggggaattcg gtccttgacc tcctcgt          27

<210> SEQ ID NO 38
<211> LENGTH: 30
<212> TYPE: DNA
<213> ORGANISM: Artificial
<220> FEATURE:
<223> OTHER INFORMATION: Primer sequence

<400> SEQUENCE: 38
cttgaattcc taggtctcat aggttgcatc       30

<210> SEQ ID NO 39
<211> LENGTH: 27
<212> TYPE: DNA
<213> ORGANISM: Artificial
<220> FEATURE:
<223> OTHER INFORMATION: Primer sequence

<400> SEQUENCE: 39
taagaattct cgtttccgga aacatgg          27

<210> SEQ ID NO 40
<211> LENGTH: 27
<212> TYPE: DNA
<213> ORGANISM: Artificial
<220> FEATURE:
<223> OTHER INFORMATION: Primer sequence

<400> SEQUENCE: 40
taaagatcta actggggtga agggatt          27

IMMUNOASSAY OF COFILIN 1 PROTEIN

TECHNICAL FIELD

The present invention relates to an immunoassay of cofilin 1 protein, an anti-cofilin 1 monoclonal antibody, a method for determining whether or not gastrointestinal cancer is developing, and a kit for cofilin 1 protein quantification.

BACKGROUND ART

Cofilin 1 (cofilin, non-muscle isoform 18 kDa phosphoprotein) protein is a cytoskeleton binding protein belonging to the ADF/COFILIN family and is one of the most highly conserved proteins among mammals. The amino acid sequence of the cofilin 1 protein has been determined for humans, mice, rats, chimpanzees, cattle, dogs, and the like, and is known to show 98% or higher identity among these species. It has been revealed that the cofilin 1 protein is involved in various biological phenomena including regulation of cell morphology and motility (Non-patent Literature 1), cytokinesis (Non-patent Literature 2), endocytosis (Non-patent Literature 3), and the like. Furthermore, the protein is also expressed at high levels in cancer tissues and cancer cells from lung cancer (Non-patent Literature 4), cancer of pancreas (Non-patent Literature 5), breast cancer (Non-patent Literature 6), ovarian cancer (Non-patent Literature 7) or hepatic cancer (Non-patent Literature 8). Involvement of the cofilin 1 protein in the progression of cancer has also been reported (Non-patent Literature 9).

PRIOR ART LITERATURE

Non-patent Literature

Non-patent Literature 1: Bugyi B. et al., 2010, Annual Review of Biophysics, Vol. 39, p. 449-470
Non-patent Literature 2: Kaji N. et al., 2008, Journal of Biological Chemistry, Vol. 283, p. 4983-4992
Non-patent Literature 3: Okreglak V. et al., 2007, The Journal of Cell Biology, Vol. 178, p. 1251-1264
Non-patent Literature 4: Keshamouni V G. et al., 2006, Journal of Proteome Research, Vol. 5, p. 1143-1154
Non-patent Literature 5: Sinha P. et al., 1999, Electrophoresis, Vol. 20, p. 2952-2960
Non-patent Literature 6: Zhang Y. et al., 2010, The Journal of International Medical Research, Vol. 38, p. 1042-1048
Non-patent Literature 7: Martoglio A. et al., 2000, Molecular Medicine, Vol. 6, p. 750-765
Non-patent Literature 8: Ding S. et al., 2004, Proteomics, Vol. 4, p. 982-994
Non-patent Literature 9: Yamaguchi H. et al. 2007, Biochemica et Biophysica Acta, Vol. 1773, p. 642-652

SUMMARY OF THE INVENTION

Problem to be Solved by the Invention

The present inventors have found in recent years that the blood levels of the cofilin 1 protein are elevated in early gastric cancer patients, and thus have developed a method for detecting gastric cancer, by which gastric cancer can be detected at an early stage using the cofilin 1 protein, or a mutant and/or a fragment of the cofilin 1 protein as a diagnostic marker useful for early detection of gastric cancer. If the quantification of the cofilin 1 protein becomes possible, this can be expected to lead to early detection and effective clinical treatment for gastrointestinal cancer including gastric cancer.

However, existing methods for detecting the cofilin 1 protein are limited to non-quantitative immunoassays with low sensitivity using such as the Western blot method. Development of a new immunoassay for clinical application remains as an unsolved problem.

Hence, an object of the present invention is to provide an immunoassay for quantitatively detecting cofilin 1 protein with high sensitivity.

Means for Solving the Problem

As a result of intensive studies to achieve the above object, the present inventors have found that the cofilin 1 protein can be quantitatively detected with high sensitivity by combining 2 or more types of monoclonal antibody, which separately specifically recognize epitopes that are present on different specific peptide regions of the amino acid sequence constituting the cofilin 1 protein, and then by immunologically measuring cofilin 1 and/or a fragment thereof. The present invention has been completed based on the above findings and provides the following (1) to (21).

(1) An anti-cofilin 1 monoclonal antibody or a fragment thereof, which specifically recognizes an epitope that is present in any one of the following peptide regions:
a) a peptide region comprising at least the amino acid sequence shown in SEQ ID NO: 5 in the amino acid sequence shown in SEQ ID NO: 1;
b) a peptide region having a deletion, a substitution, or an addition of 1 or several amino acids with respect to the amino acid sequence of the peptide region of a) above; and
c) a peptide region having 90% or more identity with the amino acid sequence of the peptide region of a) above.

(2) The anti-cofilin 1 monoclonal antibody or a fragment thereof according to (1), wherein in the light chain, CDR1 comprises the sequence shown in SEQ ID NO: 8, CDR2 comprises the sequence shown in SEQ ID NO: 9, and CDR3 comprises the sequence shown in SEQ ID NO: 10, and in the heavy chain, CDR1 comprises the sequence shown in SEQ ID NO: 11, CDR2 comprises the sequence shown in SEQ ID NO: 12, and CDR3 comprises the sequence shown in SEQ ID NO: 13.

(3) The anti-cofilin 1 monoclonal antibody or a fragment thereof according to (1), wherein in the light chain, CDR1 comprises the sequence shown in SEQ ID NO: 14, CDR2 comprises the sequence shown in SEQ ID NO: 15, and CDR3 comprises the sequence shown in SEQ ID NO: 16, and in the heavy chain, CDR1 comprises the sequence shown in SEQ ID NO: 17, CDR2 comprises the sequence shown in SEQ ID NO: 18, and CDR3 comprises the sequence shown in SEQ ID NO: 19.

(4) An anti-cofilin 1 monoclonal antibody or a fragment thereof, which specifically recognizes an epitope that is present in any one of the following peptide regions:
a) a peptide region comprising at least the amino acid sequence shown in SEQ ID NO: 6 in the amino acid sequence shown in SEQ ID NO: 1.
b) a peptide region having a deletion, a substitution, or an addition of 1 or several amino acids with respect to the amino acid sequence of the peptide region of a) above; and
c) a peptide region having 90% or more homology with the amino acid sequence of the peptide region of a) above.

(5) The anti-cofilin 1 monoclonal antibody or a fragment thereof according to (4), wherein in the light chain, CDR1 comprises the sequence shown in SEQ ID NO: 20, CDR2 comprises the sequence shown in SEQ ID NO: 21, and CDR3 comprises the sequence shown in SEQ ID NO: 22, and in the heavy chain, CDR1 comprises the sequence shown in SEQ ID NO: 23, CDR2 comprises the sequence shown in SEQ ID NO: 24, and CDR3 comprises the sequence shown in SEQ ID NO: 25.

(6) An anti-cofilin 1 monoclonal antibody or a fragment thereof, which specifically recognizes an epitope that is present in any one of the following peptide regions:
a) a peptide region comprising at least the amino acid sequence shown in SEQ ID NO: 7 in the amino acid sequence shown in SEQ ID NO: 2;
b) a peptide region having a deletion, a substitution, or an addition of 1 or several amino acids with respect to the amino acid sequence of the peptide region of a) above; and
c) a peptide region having 90% or more identity with the amino acid sequence of the peptide region of a) above.

(7) The anti-cofilin 1 monoclonal antibody or a fragment thereof according to (6), wherein in the light chain, CDR1 comprises the sequence shown in SEQ ID NO: 26, CDR2 comprises the sequence shown in SEQ ID NO: 27, and CDR3 comprises the sequence shown in SEQ ID NO: 28, and in the heavy chain, CDR1 comprises the sequence shown in SEQ ID NO: 29, CDR2 comprises the sequence shown in SEQ ID NO: 30, and CDR3 comprises the sequence shown in SEQ ID NO: 31.

(8) An immunoassay of cofilin 1 protein, comprising measuring cofilin 1 and/or a fragment thereof in a sample using 2 or more types of anti-cofilin 1 monoclonal antibody and/or fragments thereof that specifically recognize different epitopes on the amino acid sequence of the cofilin 1 protein.

(9) The immunoassay according to (8), wherein the above different epitopes are present in the peptide regions consisting of the amino acid sequences shown in SEQ ID NO: 1 and/or 2.

(10) The immunoassay according to (9), wherein the above different epitopes are present in a peptide region comprising at least the amino acid sequence shown in SEQ ID NO: 3 in the peptide region consisting of the amino acid sequence shown in SEQ ID NO: 1, and/or a peptide region comprising at least the amino acid sequence shown in SEQ ID NO: 4 in the peptide region consisting of the amino acid sequence shown in SEQ ID NO: 2.

(11) The immunoassay according to (9), wherein the above different epitopes are present in the peptide regions comprising at least the amino acid sequences shown in SEQ ID NO: 5 and/or 6 in the peptide region consisting of the amino acid sequence shown in SEQ ID NO: 1, and/or a peptide region comprising at least the amino acid sequence shown in SEQ ID NO: 7 in the peptide region consisting of the amino acid sequence shown in SEQ ID NO: 2.

(12) The immunoassay according to (8), wherein the above different epitopes are separately present in two peptide regions selected from the peptide regions consisting of the amino acid sequences shown in SEQ ID NOS: 5 to 7.

(13) The immunoassay according to (9), wherein the above different epitopes are present in a peptide region consisting of 6 or more and 21 or less continuous amino acids in the peptide regions consisting of the amino acid sequences shown in SEQ ID NO: 1 and/or 2.

(14) The immunoassay according to (8), wherein the above 2 or more types of anti-cofilin 1 monoclonal antibody and/or fragments thereof are selected from the anti-cofilin 1 monoclonal antibodies or fragments thereof of (2), (3), (5), and (7).

(15) The immunoassay according to (14), wherein the two types of anti-cofilin 1 monoclonal antibody and/or fragment thereof constitute any one of the following combinations of anti-cofilin 1 monoclonal antibodies and/or fragments thereof:
a) a combination of the anti-cofilin 1 monoclonal antibodies and/or the fragments thereof separately described in (2) and (5);
b) a combination of the anti-cofilin 1 monoclonal antibodies and/or fragments thereof separately described in (2) and (7);
c) a combination of the anti-cofilin 1 monoclonal antibodies and/or fragments thereof separately described in (3) and (5); and
d) a combination of the anti-cofilin 1 monoclonal antibodies and/or fragments thereof separately described in (5) and (7).

(16) The immunoassay according to any one of (8) to (15), wherein the sample is blood, urine, cell supernatant, cell extract, tissue extract, gastric juice, saliva, lymph fluid, lacrimal fluid, or seminal fluid.

(17) A method for determining whether or not gastrointestinal cancer is developing, comprising the steps of:
measuring the amounts of the cofilin 1 protein and/or a fragment thereof in a sample derived from a subject and a healthy subject using the immunoassay of any one of (8) to (16);
comparing the amounts of the cofilin 1 protein and/or a fragment thereof measured in the above measurement step, and then determining that the subject is affected by gastrointestinal cancer if the amount of the cofilin 1 protein and/or a fragment thereof in the subject is statistically significantly higher than that of the healthy subject.

(18) The determination method according to (17), wherein the gastrointestinal cancer is early gastrointestinal cancer.

(19) The determination method according to (17) or (18), wherein the gastrointestinal cancer is gastric cancer.

(20) A kit for cofilin 1 protein quantification, containing 2 or more types of anti-cofilin 1 monoclonal antibody and/or fragments thereof, which specifically recognize different epitopes of the cofilin 1 protein.

(21) The kit according to (20), containing 2 or more types of the anti-cofilin 1 monoclonal antibody or the fragments thereof of any one of (1) to (7).

This description includes the disclosure of the description and drawings of Japanese Patent Application No. 2010-274879, which is base of the priority of the present application.

Effects of the Invention

According to the immunoassay of the present invention, the cofilin 1 protein in a sample can be quantitatively detected with high sensitivity compared with conventional methods. Furthermore, immunoassay can be conveniently completed with simple experimental procedures.

Moreover, according to the method of the present invention for determining whether or not gastrointestinal cancer is developing, whether or not a subject is affected by gastrointestinal cancer can be determined at an early stage by measuring the amount of cofilin 1 contained in a sample such as blood of a subject.

BRIEF DESCRIPTION OF THE DRAWINGS

FIG. 4 shows the results of evaluating the detection sensitivity by sandwich ELISA for measurement of the cofilin 1 protein. FIG. 4B is a graph showing an expanded view of the circular broken-line portion in FIG. 4A. In FIG. 4B, the value indicated by an arrow is the minimum detection limit of the ELISA method.

EMBODIMENTS FOR CARRYING OUT THE INVENTION

Figure 1:
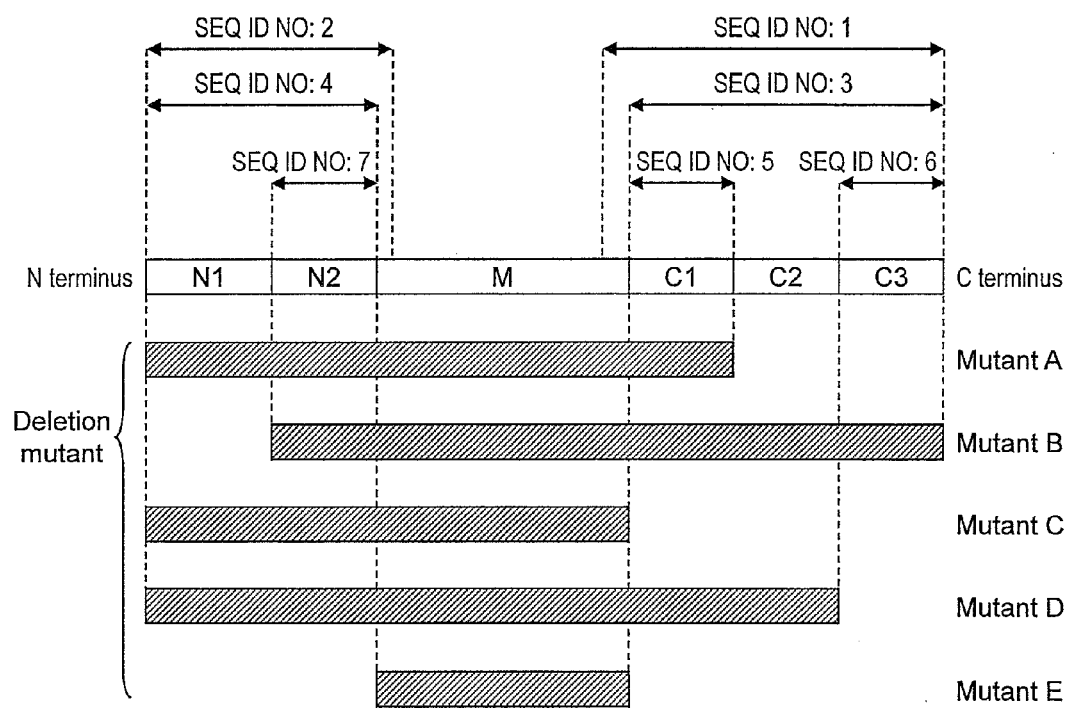
FIG. 1 shows the primary structures of deletion mutants used for epitope analysis, and each peptide region and the sequence identification number of the amino acid sequence thereof.

1. Anti-cofilin 1 Monoclonal Antibody and Fragment Thereof

A 1$^{st}$ embodiment of the present invention relates to an anti-cofilin 1 monoclonal antibody and a fragment thereof.

1-1. Anti-cofilin 1 Monoclonal Antibody

"Cofilin 1" includes the human cofilin 1 protein consisting of the amino acid sequence under. GenBank accession NP_005498.1 or a natural mutant thereof, or mammalian orthologs or natural mutants thereof showing 95% or more homology with the human cofilin 1 protein, such as a rat cofilin 1 protein consisting of the amino acid sequence under GenBank accession NP_058843, a mouse cofilin 1 protein consisting of the amino acid sequence under GenBank accession NP_031713.1, a chimpanzee cofilin 1 protein consisting of the amino acid sequence under GenBank accession NP_001170183.1, a cattle cofilin 1 protein consisting of the amino acid sequence under GenBank accession NP_001015655, or a dog cofilin 1 protein consisting of the amino acid sequence under GenBank accession NP_533231.1.

Here, the term "natural mutant" refers to a mutant existing in nature, such as a mutant having a deletion, a substitution, or an addition of one or several amino acids with respect to the above amino acid sequences, and a mutant having 90% or more, 92% or more or 94% or more, preferably 95% or more, more preferably about 97% or more, and further preferably about 99% or more identity with the above amino acid sequences. The term "sequence identity" is the percentage (%) of the number of identical amino acid residues in an amino acid sequence with respect to the total number of amino acid residues (including the number of gaps) of the other amino acid sequence, when gaps are introduced or not introduced so as to maximize the agreement between the two amino acid sequences aligned. The term "several" refers to integers between 2 and 10, such as integers of 2 to 7, 2 to 5, 2 to 4, and 2 to 3. Specific examples of a natural mutant include mutants based on polymorphism such as SNP (single nucleotide polymorphism) and splice mutants. The above substitution is preferably conservative amino acid substitution. If it is conservative amino acid substitution, the relevant mutant can have a structure or properties substantially equivalent to the cofilin 1 protein having any one of the above amino acid sequences. The conservative amino acids include nonpolar amino acids (glycine, alanine, phenylalanine, valine, leucine, isoleucine, methionine, proline, and tryptophan) and polar amino acids (amino acids other than nonpolar amino acids), charged amino acids (acidic amino acids (aspartic acids and glutamic acid) and basic amino acids (arginine, histidine, and lysine)) and uncharged amino acids (amino acids other than charged amino acids), aromatic amino acids (phenylalanine, tryptophan, and tyrosine), branched amino acids (leucine, isoleucine, and valine), and aliphatic amino acids (glycine, alanine, leucine, isoleucine, and valine).

The term "monoclonal antibody" as used herein refers to a single immunoglobulin, or a polypeptide comprising a framework region (hereinafter, referred to as "FR") thereof and a complementarity determining region (hereinafter, referred to as "CDR"), which is capable of specifically recognizing and binding to a specific antigen. Therefore, the term "anti-cofilin 1 monoclonal antibody" of the present invention refers to a polypeptide capable of specifically recognizing and binding to the cofilin 1 protein. The expression "specifically recognizing and binding to" means that a polypeptide has no or extremely weak cross-reactivity and neither recognizes nor binds or almost never recognizes and binds to antigens other than a target antigen.

A typical immunoglobulin molecule is composed as a tetramer in which two sets of polypeptide chains referred to as a heavy chain and a light chain are interconnected via disulfide bonds. The heavy chain consists of the N terminal heavy chain variable region (H chain V region, hereinafter, referred to as "VH") and the C terminal heavy chain constant region (H chain C region, hereinafter, referred to as "CH"). The light chain consists of the N terminal light chain variable region (L chain V region, hereinafter, referred to as "VL") and the C terminal light chain constant region (L chain C region, hereinafter, referred to as "CL"). VH and VL are particularly important in that VH and VL are involved in antibody binding specificity. VH and VL each consists of about 110 amino acid residues and contains three CDRs (CDR1, CDR2, CDR3) directly involved in binding specificity with an antigen and four FRs (FR1, FR2, FR3, FR4) that function as a framework structure of the variable region. CDRs are known to form a three-dimensional structure with an antigen molecule, so as to determine antibody specificity (E. A. Kabat et al, 1991, Sequences of proteins of immunological interest, Vol. 1, eds. 5, NIH publication). Whereas the amino acid sequences of constant regions are almost the same among intraspecies antibodies, the amino acid sequences of CDRs have high variability among antibodies, and thus CDRs are also referred to as hyper variable regions. In a variable region, the above CDRs and FRs are placed in order of, from the amino acid terminus to the carboxy terminal direction, FR1, CDR1, FR2, CDR2, FR3, CDR3, and then FR4. Within an immunoglobulin molecule, VL and VH face each other to form a dimer, so as to form an antigen binding site. Examples of known immunoglobulin classes include IgG, IgM, IgA, IgE, and IgD. The antibody of the present invention may be of any class. A preferable class is IgG.

The anti-cofilin 1 monoclonal antibody of the present invention is characterized by specifically recognizing an epitope that is present in: (1) a peptide region comprising at least the amino acid sequence shown in SEQ ID NO: 5 or 6 in the amino acid sequence shown in SEQ ID NO: 1; (2) a peptide region comprising at least the amino acid sequence shown in SEQ ID NO: 7 in the amino acid sequence shown in SEQ ID NO: 2; (3) a peptide region having a deletion, a substitution, or an addition of 1 or several amino acids with respect to the amino acid sequence of the peptide region of (1)

or (2) above; or (4) a peptide region having 90% or more identity with the amino acid sequence of the peptide region of (1) or (2) above.

The amino acid sequence shown in SEQ ID NO: 1 is the amino acid sequence of the C terminal peptide region (C-terminal 5 amino acids in M region and C1-C3 regions in FIG. 1) of the human cofilin 1 protein, corresponding to positions 122 to 166 when the initiator methionine is located at position 1. The amino acid sequence shown in SEQ ID NO: 5 is the amino acid sequence of the C1 region in FIG. 1, corresponding to positions 158 to 166 of the human cofilin 1 protein. The amino acid sequence shown in SEQ ID NO: 6 is the amino acid sequence of the C3 region in FIG. 1, corresponding to positions 127 to 146 of the human cofilin 1 protein. In the peptide region consisting of the amino acid sequence shown in SEQ ID NO: 5 or 6, an epitope effective for preparing an anti-cofilin 1 antibody with high-sensitivity is present.

Specific examples of the anti-cofilin 1 monoclonal antibody recognizing an epitope that is present in the C1 region shown in SEQ ID NO: 5 include antibody clones represented by antibody clone names 1E2 and 2C4 in Table 1 in Example 3 described later. The 1E2 clone is characterized in that, in the light chain, CDR1 consists of the sequence shown in SEQ ID NO: 8, CDR2 consists of the sequence shown in SEQ ID NO: 9, and CDR3 consists of the sequence shown in SEQ ID NO: 10, and in the heavy chain, CDR1 consists of the sequence shown in SEQ ID NO: 11, CDR2 consists of the sequence shown in SEQ ID NO: 12, and CDR3 consists of the sequence shown in SEQ ID NO: 13. Moreover, the 2C4 clone is characterized in that in the light chain, CDR1 consists of the sequence shown in SEQ ID NO: 14, CDR2 consists of the sequence shown in SEQ ID NO: 15, and CDR3 consists of the sequence shown in SEQ ID NO: 16, and in the heavy chain, CDR1 consists of the sequence shown in SEQ ID NO: 17, CDR2 consists of the sequence shown in SEQ ID NO: 18, and CDR3 consists of the sequence shown in SEQ ID NO: 19.

Specific examples of the anti-cofilin 1 monoclonal antibody recognizing an epitope that is present in the C3 region shown in SEQ ID NO: 6 include an antibody clone represented by antibody clone name of 4E12 in Table 1. The 4E12 clone is characterized in that, in the light chain, CDR1 consists of the sequence shown in SEQ ID NO: 20, CDR2 consists of the sequence shown in SEQ ID NO: 21, and CDR3 consists of the sequence shown in SEQ ID NO: 22, and in the heavy chain, CDR1 consists of the sequence shown in SEQ ID NO: 23, CDR2 consists of the sequence shown in SEQ ID NO: 24, and CDR3 consists of the sequence shown in SEQ ID NO: 25. In addition, the C3 region is composed of only 9 amino acids, and thus the C3 region likely constitutes an epitope itself. Furthermore, the amino acid sequence shown in SEQ ID NO: 2 is the amino acid sequence of the N terminal peptide region (N1 and N2 regions and N terminal 5 amino acids in M region in FIG. 1) of the human cofilin 1 protein, corresponding to positions 1 to 54 when initiator methionine is located at position 1. The amino acid sequence shown in SEQ ID NO: 7 is the amino acid sequence of the N2 region in FIG. 1, corresponding to a sequence of positions 29 to 49 of the human cofilin protein. In the peptide region consisting of the amino acid sequence shown in SEQ ID NO: 7, an epitope effective for preparing an anti-human cofilin 1 antibody with high sensitivity is present.

Specific examples of the anti-cofilin 1 monoclonal antibody recognizing an epitope in the N2 region shown in SEQ ID NO: 7 include an antibody clone represented by antibody clone name of 4F12 in Table 1. The 4F12 clone is characterized in that, in the light chain, CDR1 consists of the sequence shown in SEQ ID NO: 26, CDR2 consists of the sequence shown in SEQ ID NO: 27, and CDR3 consists of the sequence shown in SEQ ID NO: 28, and in the heavy chain, CDR1 consists of the sequence shown in SEQ ID NO: 29, CDR2 consists of the sequence shown in SEQ ID NO: 30, and CDR3 consists of the sequence shown in SEQ ID NO: 31.

Antibodies useful in the present invention may be derived from all animal sources including birds and mammals. Examples thereof include mice, rats, guinea pigs, rabbits, goats, donkeys, sheep, camels, horses, chickens and humans. In general, antibodies of mice, rats, or rabbits are preferably used.

Moreover, the "antibody" in the present invention may be a multispecific antibody. The term "multispecific antibody" refers to a multivalent antibody; that is, an antibody having multiple antigen binding sites within one molecule, in which each antigen binding site binds to a different epitope. In the case of a bispecific antibody such as IgG having two antigen binding sites, each antigen binding site binds to a different epitope. In the present invention, a multispecific antibody has antigen binding sites, so as to be able to bind to different epitopes that are present in the cofilin 1 protein. These antibodies can be obtained by artificially altering IgG or the like by a known method using a DNA recombination technique.

1-2. Anti-cofilin 1 Monoclonal Antibody Fragment

The term "a fragment thereof" in "monoclonal antibody or a fragment thereof" as used herein refers to a partial fragment of the above monoclonal antibody, and specifically refers to a polypeptide chain or a complex thereof having activity substantially equivalent to the antigen-specific binding activity of the antibody. For example, it may involve an antibody portion containing at least one antigen binding site described above; that is, a polypeptide chain or a complex thereof having at least a set of VL and VH. Specific examples thereof include many sufficiently characterized antibody fragments or the like obtained by cleaving an immunoglobulin with various peptidases. More specific examples thereof include Fab, F(ab')$_2$, and Fab'. Fab is a fragment that is generated by cleaving an IgG molecule with papain at a site closer to the N-terminal side than to the hinge disulfide bonds, which is composed of a polypeptide consisting of VH and CH1 adjacent to VH among 3 domains (CH1, CH2, CH3) constituting CH and a light chain. F(ab')$_2$ is a Fab' dimer that is generated by cleaving an IgG molecule with pepsin at a site closer to the C-terminal side than to the hinge disulfide bonds. Fab' has an H chain that is somewhat longer than that of Fab since Fab' contains the hinge region, but Fab has a structure substantially equivalent to that of Fab (Fundamental Immunology, Paul ed., 3d ed., 1993.). Fab' can be obtained by reducing F(ab')$_2$ under mild conditions, so as to cleave the hinge disulfide bonds. All of these antibody fragments contain antigen binding sites and are capable of specifically binding to antigens (specifically, in the present invention, the cofilin 1 protein or a fragment thereof).

The monoclonal antibody fragment of the present invention can be chemically synthesized or synthesized using a recombinant DNA technique. Examples thereof are antibody fragments that are newly synthesized using the recombinant DNA technique. Specific examples of the monoclonal antibody fragment include, but are not limited to, a monomeric polypeptide molecule prepared by artificially linking one or more VLs and one or more VHs of the monoclonal antibody of the present invention via a linker peptide or the like having an appropriate length and an appropriate sequence, and a multimeric polypeptide thereof. Examples of such a polypeptide include single-stranded Fv (scFv: single chain Fragment of variable region)(see Pierce catalog and Handbook, 1994-1995, Pierce Chemical co., Rockford, Ill.), and synthetic antibodies such as a diabody, a triabody, or a tetrabody. In an immunoglobulin molecule, VL and VH are generally located on separate polypeptide chains (L chain and H chain, respectively). Single-stranded Fv is a synthetic antibody fragment prepared by ligating these variable regions with a flexible linker having a sufficient length, so as to have a structure in which one polypeptide chain contains VL and VH. Within single-stranded Fv, both variable regions can self-assemble to form one functional antigen binding site. Single-stranded Fv can be obtained by incorporating recombinant DNA encoding the Fv into a phage genome using a known technique for expression. A diabody is a molecule having a structure based on the dimeric structure of single-stranded Fv (Holliger et al, 1993, Proc. Natl. Acad. Sci. U.S.A., 90: 6444-6448). For example, when the length of the above linker is shorter than about 12 amino acid residues, two variable sites within the single-stranded Fv are unable to self-assemble. However, through the formation of a diabody and specifically interaction between the two single-stranded Fvs, VL of one of the Fv chains becomes possible to self-assemble with VH of the other Fv chain, so that two functional antigen binding sites can be formed (Marvin et al, 2005, Acta Pharmacol. Sin., 26: 649-658). Furthermore, a cysteine residue is added to the C terminus of single-stranded $F_v$, making it possible to form a disulfide bond of the two $F_v$ chains, and thus a stable diabody can also be formed (Alafsen et al, 2004, Prot. Engr. Des. Sel., 17: 21-27). As described above, a diabody is a divalent antibody fragment. The two antigen binding sites thereof are not required to bind to the same epitope and they may have bispecificity by which they recognize and specifically bind to different epitopes. A triabody and a tetrabody have, similarly to a diabody, a trimeric structure and a terameric structure, respectively, on the basis of the single-stranded Fv structure. Such a triabody and a tetrabody are trivalent and tetravalent antibody fragments, respectively, or may be multispecific antibodies. Moreover, the antibody fragment of the present invention may be an antibody fragment that is identified using a phage display library (e.g., see McCafferty et al., 1990, Nature, Vol. 348, 522-554) and have antigen binding capacity. In addition to the literature, see Kuby, J., Immunology, $3^{rd}$ Ed., 1998, W. H. Freeman & Co., New York, for example.

1-3. Other Characteristics of Anti-cofilin 1 Monoclonal Antibody and Fragment Thereof The antibody or a fragment thereof of the present invention can be modified. The modification as used herein includes any of functional modification (e.g., glycosylation) required for the antibody or a fragment thereof of the present invention to have activity of specifically binding to the cofilin 1 protein, and labeling required for detection of the antibody or a fragment thereof of the present invention. Examples of the aforementioned labels for the antibodies include fluorescent dyes (FITC, rhodamine, Texas Red, Cy3, and Cy5), fluorescent proteins (e.g., PE, APC, and GFP), enzymes (e.g., horseradish peroxidase, alkaline phosphatase, and glucose oxidase), and biotin or (strept)avidin. Furthermore, glycosylation of the antibody of the present invention may be altered to adjust the antibody affinity for a target antigen. Such modification can be achieved by, for example, changing one or more glycosylation sites within the antibody sequence. More specifically, one or more amino acid substitutions are introduced into an amino acid sequence constituting one or more glycosylation sites within FR, so as to remove the glycosylation sites, so that the loss of glycosylation at the sites can be realized, for example. Such deglycosylation is effective for increasing antibody affinity for an antigen (U.S. Pat. Nos. 5,714,350 and 6,350,861).

A monoclonal antibody or a fragment thereof to be used in the present invention is preferably verified in advance for cross-reactivity with other antigens (proteins or fragments thereof) before use in order to confirm the specificity to the cofilin 1 protein or a fragment thereof. Regarding the antibody or a fragment thereof of the present invention, examples of an antigen, for which cross-reactivity should be confirmed, include, proteins belonging to the ADF/COFILIN family and particularly a cofilin 2 protein structurally analogous to the cofilin 1 protein. The cross-reactivity of an antibody or a fragment thereof to be used in the present invention is more preferably confirmed in advance for other proteins sharing a common partial structure with the cofilin 1 protein, other than the above proteins. For confirmation of cross-reactivity, an ELISA method using the cofilin 1 protein as an antigen can be employed. By coexisting with another antigen protein to be confirmed for cross-reactivity at a reaction site of an antibody to be tested for reaction specificity; that is, a site for reaction of an anti-cofilin 1 monoclonal antibody and a fragment thereof with the cofilin 1 protein, cross-reactivity can be confirmed based on observation of the competitive state of the two. Screening can be rapidly performed by such a method for confirmation of cross-reactivity using the principle of competitive inhibition, since the preparation of reaction systems is not required for all antigens.

1-4. Method for Preparing Anti-cofilin 1 Monoclonal Antibody and Hybridoma

The anti-cofilin 1 monoclonal antibody of the present invention or a hybridoma producing the antibody can be prepared by the method described below. Examples of the method are not limited to this method and the anti-cofilin 1 monoclonal antibody and such a hybridoma can also be prepared by all other methods known in the art.

1-4-1. Method for Preparing Anti-cofilin 1 Monoclonal Antibody

Methods for preparing an anti-cofilin 1 monoclonal antibody specifically binding to an epitope that is present in a peptide region consisting of any one of the amino acid sequences shown in SEQ ID NOS: 1 to 7 from among amino acid sequences constituting the cofilin 1 protein are: a method that involves preparing a monoclonal antibody using the full-length cofilin 1 protein as an immunogen, and then screening for an antibody that specifically binds to a peptide region consisting of any one of the amino acid sequences shown in SEQ ID NOS: 1 to 7; and a method for preparing a monoclonal antibody using in advance a peptide that consists of a cofilin 1 protein fragment shown in SEQ ID NOS: 1 to 7, as an immunogen.

(1) Preparation of Cofilin 1 Protein

The cofilin 1 protein to be used as an immunogen (antigen) can be prepared by the following method, for example.

The cofilin 1 protein may be of a natural, a recombinant, or a synthetic cofilin 1 protein synthesized by, e.g., peptide synthesis, chemically synthesizing the whole or a part of the amino acid sequence. A natural cofilin 1 protein can be recovered from a sample such as a body fluid (e.g., blood or urine) or a culture supernatant of cultured cells by known protein separation and purification techniques such as gel chromatography, ion exchange chromatography, or affinity chromatography. A recombinant cofilin 1 protein can be expressed in microorganisms, insect cells, or animal cells into which DNA encoding the protein has been introduced and then recovered from the cells using known protein separation and purification techniques. A synthetic cofilin 1 protein can be synthesized by a technique known in the art (e.g., a solid phase peptide synthesis method) using, for example, published information in amino acid sequence of cofilin 1 protein. To the thus synthesized cofilin 1 protein, a carrier protein such as KLH (keyhole lympet hemocyanin), OVA (ovalbumin), or BSA (bovine serum albumin) may be ligated.

When the cofilin 1 protein fragments shown in SEQ ID NOS: 1 to 7 are used as immunogens, any one of a natural cofilin 1 protein fragment, a recombinant cofilin 1 protein fragment, or a synthetic cofilin 1 protein fragment can also be used herein. As such a cofilin 1 protein fragment, an oligo peptide or a polypeptide comprising, in the sequences shown in SEQ ID NOS: 1 to 7, continuous 6 or more, 7 or more, 8 or more, 9 or more, 10 or more, 11 or more, 12 or more, 13 or more, 14 or more, 15 or more, 16 or more, 17 or more, 18 or more, 19 or more, 20 or more, 21 or more, 22 or more, or 23 or more amino acid residues can be used as an antigen.

When a natural cofilin 1 protein fragment is used as an immunogen, for example, the purified cofilin 1 protein is treated with appropriate protease such as trypsin, the peaks are fractionated with a reverse phase column, the amino acid sequence of a peptide contained in each peak was determined with a mass spectrometer, and then a peak corresponding to a partial sequence shown in SEQ ID NOS: 1 to 7 or a part thereof can be used as an immunogen.

When partial amino acid sequences of a recombinant cofilin 1 protein are used as immunogens, among the above DNA sequences encoding the cofilin 1 protein, the partial amino acid sequences shown in SEQ ID NOS: 1 to 7 or partial DNA sequences encoding portions thereof are inserted to expression vectors in a manner similar to that for preparation of the full-length cofilin 1 protein, the vectors are introduced into various cells, and thus recombinant cofilin 1 proteins comprising the partial amino acid sequences shown in SEQ ID NOS: 1 to 7 or portions thereof can be obtained.

Preparation of recombinant cofilin 1 protein fragments (hereinafter, referred to as "cofilin 1 protein fragments") shown in SEQ ID NOS: 1 to 7 is as described in detail below.

(a) Preparation of Polynucleotide Encoding Recombinant Cofilin 1 Protein Fragment As a vector to be used for expression of a cofilin 1 protein fragment, a phage or a plasmid capable of autonomously replicating in a host microorganism can be used. Examples of such a plasmid include *Escherichia coli*-derived plasmids (e.g., pET30a, pGEX6p, pUC118, pUC119, pUC18, and pUC19), *Bacillus subtilis*-derived plasmids (e.g., pUB110 and pTP5) and yeast-derived plasmids (e.g., YEp13, YEp24, and YCp50). Examples of a phage include λ phages (e.g., λ gt11 and λ ZAP). Furthermore, animal viruses such as a vaccinia virus and insect virus vectors such as baculovirus can also be used herein.

A method that is employed for insertion of a polynucleotide encoding a cofilin 1 protein fragment into the above vector involves, for example, cleaving the purified polynucleotide with an appropriate restriction enzyme, and then ligating the resultant into a vector cleaved with an appropriate restriction enzyme, with the use of DNA ligase or the like.

(b) Introduction of Cofilin 1 Protein Fragment Expression Vector into Host

The obtained cofilin 1 protein fragment expression vector is introduced into a host capable of expressing the expression vector, and then a cofilin 1 protein fragment-expressing transformant is obtained. A host to be used herein is not particularly limited, as long as it is a host appropriate for a vector to be used herein and can express the cofilin 1 protein. For example, bacteria (e.g., *Escherichia coli* and *Bacillus subtilis*), yeast, insect cells, animal cells (COS cells and CHO cells (Journal of immunology, 1998, Vol. 160, 3393-3402)), and the like are preferably used. A method for introducing the above vector into bacteria is not particularly limited, as long as it is a known method for introducing the vector into bacteria. Examples thereof include a heat shock method, a method using calcium ion, and an electroporation method. All of these techniques are known in the art and described in various literatures. For example, see Sambrook, J. et. Al., 1989, Molecular Cloning: A Laboratory Manual Second Ed., Cold Spring Harbor Laboratory Press, Cold Spring Harbor, N.Y. Also, for transformation of animal cells, a lipofectin method (PNAS, 1989, Vol. 86, 6077), (PNAS, 1987, Vol. 84, 7413), an electroporation method, a calcium phosphate method (Virology, 1973, Vol. 52, 456-467), a DEAE-Dextran method and the like are preferably employed herein.

When a bacterium is used as a host, a cofilin 1 protein fragment expression vector is preferably autonomously replicable within the bacterium, and at the same time is preferably composed of a promoter sequence, a ribosome binding sequence, a DNA sequence encoding a cofilin 1 protein fragment, and a transcription termination sequence. Also, a gene encoding a promoter-controlling regulatory factor may also be contained. Any promoter can be used herein as long as it is capable of functioning in a host such as *Escherichia coli*.

When eukaryotic cells such as yeast, animal cells, or insect cells are used as host cells, a cofilin 1 protein fragment-expressing transformant can be obtained according to techniques known in the art similarly. A cofilin 1 protein fragment expression vector to be used in eukaryotic cells contains, in addition to a promoter sequence and a DNA sequence encoding a cofilin 1 protein fragment, a cis element, such as an enhancer, splicing signals (e.g., donor site, acceptor site, and branch point), a polyA addition signal, a selection marker sequence, a ribosome binding sequence (SD sequence), and the like that are ligated as necessary.

(c) Culture of Transformant and Expression of Recombinant Cofilin 1 Protein Fragment Subsequently, the above prepared transformant is cultured. A method for culturing transformant in a medium is according to a general method that is employed for culturing a host. For example, when a bacterium is used as a host, a medium contains a carbon source, a nitrogen source, inorganic salts, and the like that are assimilable by bacteria and enables bacterial growth and proliferation. The examples of such a medium are not particularly limited. Either natural medium or synthetic medium can be used herein. A more specific example thereof is, but is not limited to, an LB medium. Furthermore, for selective culture of a transformant, antibiotics such as ampicillin or tetracycline may be added into a medium if necessary. Culture is generally performed under aerobic conditions such as aeration-agitation culture at 37° C. for 6 to 24 hours. During the culture period, the pH is preferably maintained at around neutral pH. pH adjustment is performed using inorganic or organic acid, an alkaline solution, or the like. When a transformant is an animal cell such as a CHO cell, host cells may be seeded into DMEM (Gibco) at $1 \times 10^5$ cells/mL and then cultured in a 5% $CO_2$ incubator at 37° C. Antibiotics such as ampicillin or tetracycline may also be added to a medium during culture, if necessary.

When the above cofilin 1 protein fragment expression vector is a protein expression-inducing vector containing a protein expression control system (e.g., when a host is a bacterium, examples of the system are a repressor gene and an operator, etc.), the above transformant should be subjected to predetermined treatment so as to induce the expression of the cofilin 1 protein fragment. Methods for inducing expression differ depending on protein expression control systems contained in vectors, and thus induction treatment appropriate for the relevant system is performed. For example, a protein expression control system that is most generally employed for a protein expression-inducing vector using a bacterium as a host comprises a lac repressor gene and a lac operator. This system can induce expression via IPTG (isopropyl-1-tio-(β-D-galactoside) treatment. For expression of the cofilin 1 protein of interest in a transformant having a cofilin 1 protein expression vector that contains the system, an appropriate amount of IPTG (e.g., a final concentration of 1 mM) may be added into the medium.

(d) Extraction and/or Recovery of Recombinant Cofilin 1 Protein Fragment

After culture, when a cofilin 1 protein fragment is produced within microorganisms or cells, microorganisms or cells are collected and then disrupted, so that the protein can be extracted. Also, when a cofilin 1 protein fragment is produced outside the microorganisms or cells, the culture solution may be directly used, or microorganisms or cells are removed by centrifugation or the like and then a supernatant may be used. Subsequently, general protein purification methods such as ammonium sulfate precipitation, gel chromatography, ion exchange chromatography, and affinity chromatography are independently used or used in an appropriate combination thereof, so that the cofilin 1 protein can be isolated and purified from the culture product. Obtainment of a cofilin 1 protein fragment may be confirmed by SDS-polyacrylamide gel electrophoresis or the like.

(2) Preparation of Anti-cofilin 1 Protein Fragment Antibody-Producing Cells

A recombinant cofilin 1 protein fragment obtained in (1) above as an immunogen is dissolved in a buffer, so as to prepare an immunogen solution. At this time, for effective immunization, an adjuvant may be added if necessary. Examples of an adjuvant include commercially available Freund's complete adjuvant (FCA) and Freund's incomplete adjuvant (FIA), which may be used independently or mixed and then used.

Next, the above-prepared immunogen solution is administered to a mammal such as a rat, a mouse (e.g., BALB/c (inbred line mouse)), or a rabbit for immunization. Examples of a method for administration of an immunogen include, but are not limited to, subcutaneous injection using FIA or FCA, intraperitoneal injection using FIA, and intravenous injection using 0.15 mol/L sodium chloride. A single dose of an immunogen is appropriately determined depending on animal types to be immunized, route of administration, and the like, ranging from about 50 μg to 200 μg per animal. Furthermore, immunization intervals are not particularly limited such that after primary immunization, a booster is performed 2 to 6 times and preferably 3 to 4 times at intervals of several days to several weeks and at intervals of preferably 1 to 4 weeks. After primary immunization, antibody titer in the serum of an immunized animal is measured by ELISA (Enzyme-Linked ImmunoSorbent Assay) or the like. When the antibody titer reaches a plateau, an immunogen is intravenously or intraperitoneally injected for final immunization. Two to 5 days and preferably 3 days after the final immunization, antibody-producing cells are collected.

1-4-2. Method for Preparing Hybridoma Producing Anti-Cofilin 1 Partial Sequence Monoclonal Antibody (1) Recovery of Antibody-Producing Cells from Immunized Animal and Cell Fusion Cell fusion of antibody-producing cells obtained from an immunized animal to myeloma cells is performed, so that a hybridoma producing a monoclonal antibody that specifically recognizes a partial sequence of the cofilin 1 protein can be prepared. Examples of antibody-producing cells include spleen cells, lymph node cells, and peripheral blood cells. Preferable examples thereof are spleen cells or local lymph node cells. As myeloma cells to be fused to antibody-producing cells, established cells derived from a mouse or the like, which are generally available, can be used. A preferable cell line to be used herein has drug selectivity and has a property such that it cannot survive in a HAT selective medium (containing hypoxanthine, aminopterin, and thymine) in an unfused state, but can grow only in a state of being fused to antibody-producing cells. Also, preferable established cells are derived from an animal of the same species or lines of an immunized animal. Specific examples of myeloma cells include BALB/c mouse-derived hypoxanthine•guanine•phosphoribosyl-transferase (HGPRT)-deficient cell lines such as the P3X62-Ag.8 cell line (ATCCTIB9), the P3X63-Ag. 8. U1 cell line (JCRB9085), the P3/NSI/1-Ag4-1 cell line (JCRB0009), the P3X63Ag8.653 cell line (JCRB0028) and the Sp2/0-Ag14 cell line (JCRB0029).

For cell fusion of the above myeloma cells to antibody-producing cells, in an animal cell culture medium such as serum-free DMEM or an RPMI1640 medium, antibody-producing cells and myeloma cells are mixed at a ratio ranging from about 1:1 to 20:1, and then a fusion reaction is conducted in the presence of a Cell fusion accelerator. As a cell fusion accelerator, polyethylene glycol or the like having an average molecular weight of 1,500 Da-4,000 Da can be used at a concentration of about 10%-80%. Moreover, if necessary, an adjunct such as dimethyl sulfoxide can be used in combination in order to increase fusion efficiency. Furthermore, antibody-producing cells and myeloma cells can be fused to each other using a commercially available cell fusion apparatus that uses electrical stimulation (e.g., electroporation) (Nature, 1977, Vol. 266, 550-552).

(2) Selection of Hybridoma of Interest

A method for selecting hybridomas producing an anti-cofilin 1 fragment monoclonal antibody of interest from cells after cell fusion treatment involves appropriately diluting a cell suspension with fetal calf serum-containing RPMI1640 medium or the like, seeding cells onto a 96-well microtiter plate at about $2 \times 10^6$ cells/well, adding a selective medium to each well, and then culturing while appropriately exchanging selective media. The temperature for culture ranges from 20° C. to. 40° C. and is preferably about 37° C. When myeloma cells are of an HGPRT-deficient cell line or a thymidine kinase (TK)-deficient cell line, only hybridomas of antibody-producing cells and myeloma cells can be selectively grown and proliferated with the use of a selective medium (HAT medium) containing hypoxanthine•aminopterin•thymidine. Thus, cells that grow around about 10 days after the initiation of culture in the selective medium can be selected as hybridomas of interest.

Hybridomas that are selected with a HAT medium are subjected to screening using as an indicator the binding activities to a natural or recombinant cofilin 1 protein or peptide regions consisting of the amino acid sequences shown in SEQ ID NOS: 1 to 7. Subsequently, hybridomas producing an antibody that has binding activity to the cofilin 1 protein are tested for cross-reactivity. Specifically, the binding activity to another ADF/COFILIN family or the like is verified, and hybridomas with acceptable cross-reactivity are selected. The term "acceptable cross-reactivity" refers to the ignorable degree of cross-reactivity in terms of application of an antibody of interest. For example, in the case of a monoclonal antibody to be used for immunoassay, if signal intensity resulting from a cross-reaction in the final measurement system can be suppressed to a level between the background level and less than 1% of signal intensity resulting from a specific reaction, it can be concluded that no cross-reaction virtually takes place.

For confirmation of reactivity to the cofilin 1 protein or cross-reactivity to another ADF/COFILIN family, for example, an ELISA method can be used. In the ELISA method, a microplate is prepared by immobilizing the cofilin 1 protein or a fragment thereof as an antigen, and then a sample prepared by appropriately diluting a culture supernatant of the above hybridoma is added to the microplate for reaction. After sufficient reaction, wells are washed, and then a labeled secondary antibody against the immunoglobulin is added for further reaction. Wells are washed again, and then the label of the secondary antibody bound to wells is finally measured, so that the binding activity of the antibody (existing in the culture supernatant) to the antigen can be quantitatively found.

Hybridomas can also be selected using recombinant DNA techniques. First, mRNA is extracted from a hybridoma group obtained according to the above method. A known method, for example, described in Example 1 may be employed for mRNA extraction. Next, cDNA of the above mRNA is obtained using oligo dT primers or random primers. PCR is carried out using the cDNA as a template and a primer set containing the nucleotide sequence of a signal sequence located upstream of a gene encoding a variable region and the nucleotide sequence on the constant region side. The thus obtained amplification product is inserted to an appropriate cloning vector for cloning, and thus a variable region gene library of an antibody produced by the hybridomas can be obtained. In a more specific example, PCR is carried out using, but not limited to, Mouse Ig Primer (Novagen), the amplification product (mouse immunoglobulin variable region cDNA) is inserted to an EcoR I site of ZERO BLUNT PCR TOPO Vector (Invitrogen) for cloning, and then the thus obtained vector group can be used as a gene library encoding variable region amino acid sequences. Subsequently, a probe is designed based on the amino acid sequence of a variable region or each CDR disclosed above in the present invention, positive clones are screened for from the above library, and thus hybridomas producing the antibody of the present invention can be selected.

(3) Antibody Production Using Hybridoma

Hybridomas in the present invention can be prepared in the form of ascites using mice, so that they can be used for antibody production. Specifically, hybridomas are intraperitoneally inoculated to mice, from which cells used for fusion partners upon hybridoma preparation are derived or nude mice, ascites are appropriately collected, and thus an ascites solution containing the antibody can be recovered. More specifically, hybridomas prepared with SP/0 cells as fusion partners are inoculated intraperitoneally to BALB/c mice 10 days after pristine inoculation, and thus an ascites solution containing the antibody can be recovered.

Furthermore, hybridomas in the present invention can be used for antibody production by culturing the hybridomas using appropriate medium. Specifically, a culture supernatant containing the antibody can be obtained by seeding hybridomas into hybridoma SFM medium (Gibco) at $1 \times 10^5$ cells/mL, culturing cells at 37° C. in a 5% $CO_2$ incubator until all hybridomas had died. The example thereof is not limited thereto.

(4) Method for Preparing Recombinant Anti-cofilin 1 Protein Fragment Monoclonal Antibody The antibody or a fragment thereof of the present invention can also be obtained by recombinant DNA procedures using the cDNA sequence encoding the amino acid sequence of a monoclonal antibody that specifically recognizes a cofilin 1 fragment disclosed in the present invention.

For example, with the use of a DNA sequence encoding the amino acid sequence that encodes a variable region of an antibody derived from the anti-cofilin 1 protein fragment monoclonal antibody-producing hybridoma obtained by the techniques in "1-4-2(2)" above, the nucleotide sequences of VH and VL are ligated to the nucleotide sequences encoding arbitrary CL and CH, respectively, and then each polynucleotide is incorporated into an appropriate expression vector. After the vector is introduced into host cells, the resultant can be expressed as a complete immunoglobulin molecule. Moreover, with the use of a CDR grafted antibody technique, the amino acid sequence of the CDR sequence, from among the amino acid sequences encoding variable regions obtained by the techniques in "1-4-2(2)" above, is incorporated into each CDR of an arbitrary immunoglobulin to result in a variable region. A polynucleotide encoding the variable region is incorporated into an appropriate expression vector, the vector is introduced into host cells, and then the resultant may be expressed as a complete immunoglobulin molecule. At this time, a heavy chain and a light chain may be expressed in the same host cell and then a dimer consisting of the heavy chain and the light chain can be produced. Specifically, for example, cells are co-transformed with a light chain expression vector and a heavy chain expression vector, and then the antibody according to the present invention can also be obtained from the transformed cells. Alternatively, a polynucleotide encoding the above amino acid sequence can be directly incorporated into an appropriate expression vector, the vector is introduced into host cells, and then the resultants can also be expressed as fragments of the immunoglobulin molecule. Alternatively, as described above, polynucleotides encoding VL and VH or a light chain and a heavy chain, respectively, comprising the above amino acid sequences are linked with an appropriate linker, and then the resultant is incorporated into a phage. Thus, the resultant can be expressed as single-stranded Fv or a synthetic antibody fragment such as a diabody. Moreover, with the use of recently developed genetic engineering techniques, genes encoding a heavy chain and a light chain are artificially shuffled using a phage display antibody technique (Brinkmann et al, 1995, J Immunol Methods, 182, 41-50, International Patent Publication WO97/13844 and WO90/02809) by which a recombinant antibody is expressed on phage surfaces, the thus diversified single-stranded Fv antibodies are expressed as phage fusion proteins, and thus specific antibodies can also be obtained.

Preparation of a polynucleotide encoding a recombinant anti-cofilin 1 protein fragment monoclonal antibody or a fragment thereof, construction of a vector into which the polynucleotide has been incorporated, and a method for introducing the vector into a host may be carried out using a recombinant DNA technique known in the art as described in 1-4-1., "Method for preparing anti-cofilin 1 monoclonal antibody" above. The recombinant anti-cofilin 1 protein antibody or a fragment thereof of interest can be obtained from a culture solution of transformed cells or from within the cells.

As immunoglobulin expression vectors, for example, plasmids, phagemids, cosmids, viral vectors (e.g., SV40 virus-based vector, EB virus based vector, and BPV based vector), and the like can be used, but examples thereof are not limited thereto. For example, a BCMGS Neo vector that is one type of BPV-based vector is a desirable vector since a foreign gene is efficiently expressed by transformation of COST cells or the like with the BCMGS Neo vector (Hajime Karasuyama "Cattle Papillomavirus Vector,", Ed., Masami Muramatsu and Hiroto Okayama, Experimental Medicine Separate Volume: Genetic Engineering Handbook, 1991, YODOSHA, 297-299).

The above vector may contain, in addition to a polynucleotide encoding an antibody or a fragment thereof, regulatory elements required for expression of such an antibody or a fragment thereof (e.g., a promoter, an enhancer, a terminator, a polyadenylation site, and a splicing site), or a selection marker, as necessary.

As hosts for transformation, in addition to hosts described in 1-4-1., "Method for preparing anti-cofilin 1 monoclonal antibody" above, SP2/0 (mouse myeloma) cells (European Journal of Cancer Research Preview (1996) Vol. 5, 512-519; Cancer Research (1990) Vol. 50, 1495-1502) are preferably used.

Host cells in the present invention containing a vector expressing an antibody or a fragment thereof are cultured according to a conventional method and thus the antibody can be produced in the culture supernatant or within host cells. Specifically, when CHO cells are used as host cells, host cells are seeded into DMEM (Gibco) at $1 \times 10^5$ cells/mL, cultured in a 5% $CO_2$ incubator at 37° C., and thus the culture supernatant containing the antibody can be obtained. When *Escherichia coli* cells are used as host cells, *E. coli* cells are seeded and cultured in general medium such as LB medium to be used for culturing *Escherichia coli*, so as to induce protein expression, and thus the antibody can be produced in a culture supernatant or within host cells.

In addition, when an antibody or a fragment thereof as an expression product contains a constant region, the product can be purified and/or recovered from a culture supernatant or a cell disruption solution using a protein A column, a protein G column, an anti-immunoglobulin antibody affinity column, or the like. Meanwhile, when an expression product is expressed in a form containing no constant region, and thus is composed of only a variable region, the above purification method cannot be applied thereto. Hence, another appropriate purification method is applied. For example, an expression product is expressed to have a structure in which a tag sequence advantageous for purification, such as a histidine tag, has been fused to the C terminus, so that purification is possible by affinity chromatography using a ligand corresponding thereto. If an expression product is not a fusion protein with a tag, it can be purified according to a conventional method for protein purification such as ammonium sulfate precipitation, ion exchange chromatography, reverse phase chromatography, gel filtration chromatography, or hydroxy apatite chromatography.

1-4-3. Confirmation of Epitope on Cofilin 1 Protein to be Recognized by the Obtained Anti-Cofilin 1 Monoclonal Antibody A sequence on the cofilin 1 protein to be specifically recognized by the obtained anti-cofilin 1 monoclonal antibody; that is, an epitope sequence can be determined by preparing various deletion mutant genes using PCR and the like based on the gene of the protein, and then analyzing the binding of the monoclonal antibody to mutant cofilin 1 proteins obtained from the mutant genes. Specifically, this is carried out by the following method. First, fragments with various lengths are prepared by deleting 10 to 400 nucleotides from the 5' terminal side, or the 3' terminal side, or both ends (the 5' terminus and the 3' terminus) of the cofilin 1 gene. These fragments are inserted into vectors and various expression vectors are constructed. Such a method for preparing gene fragments with various deletion mutations is described in "Seikagaku Jikken Koza 2 (Biochemical Experimental Lecture Series 2), Vol. 1, Idenshi Kenkyu-ho (Method for Genetic Research) II, pp. 289-305, Ed., The Japanese Biochemical Society." First, various deletion mutant proteins and the full-length cofilin 1 protein are prepared by the above method from host cells into which expression vectors of different deletion mutants and the expression vector of the full-length cofilin 1 protein have been introduced. Subsequently, the binding of the anti-cofilin 1 monoclonal antibody to various deletion mutants and the full-length protein is evaluated by an ELISA method using these proteins as antigens. When the monoclonal antibody loses the binding in a mutant prepared by introducing a deletion of a specific amino acid sequence into the full-length sequence, it can be concluded that at least a part of the region (from among the epitope sequence of the monoclonal antibody) is contained in the amino acid sequence having the relevant deletion. Moreover, the number of epitope sequences can further be narrowed down by evaluating the reactivity of the monoclonal antibody to different 2 types of and preferably 3 types of deletion mutant.

An epitope sequence on the cofilin 1 protein to be recognized by the obtained anti-cofilin 1 monoclonal antibody can also be confirmed by the following method.

First, the cofilin 1 protein subjected to reductive alkylation is reacted with an anti-cofilin 1 monoclonal antibody to form an antigen-antibody complex, followed by proteolysis using appropriate protease such as trypsin. Even subjected to proteolysis, antibodies are not easily digested with trypsin. Hence, an antigen-antibody complex can be recovered using ProteinG sepharose or the like. At this time, as a result of digestion by proteolysis with protease, antigen portions other than those protected by binding to antibodies are digested. The recovered antigen-antibody complex is analyzed by LC-MS, and thus portions protected by binding to antibodies; that is, an epitope on the cofilin 1 protein to be recognized by the antibody can be identified.

Furthermore, an epitope sequence on the cofilin 1 protein to be recognized by the anti-cofilin 1 monoclonal antibody can be confirmed by, for example, a competitive method using a synthetic peptide. First, synthetic peptides each consisting of 6 to 21 amino acids of the amino acid sequence constituting the cofilin 1 protein are prepared by a solid phase synthesis method or the like. In the above experiment for confirming the binding to the cofilin 1 protein using the ELISA method, the synthetic peptides are caused to act when the anti-cofilin monoclonal antibody is reacted with the immobilized cofilin 1 protein. When the inhibition of the binding of the anti-cofilin 1 monoclonal antibody is confirmed, it can be concluded that the amino acid sequences of the synthetic peptides are epitope sequences to be recognized by the anti-cofilin 1 monoclonal antibody.

2. Immunoassay of Cofilin 1 Protein

A $2^{nd}$ embodiment of the present invention relates to an immunoassay of cofilin 1 protein. The immunoassay of the present invention is characterized by measuring cofilin 1 and/or a fragment thereof in a sample using 2 or more types of anti-cofilin 1 monoclonal antibody and/or fragments thereof specifically recognizing different epitopes on the amino acid sequence of the cofilin 1 protein. With the use of the monoclonal antibody or a fragment thereof, measurement excellent in quantification of and detection sensitivity for the cofilin 1 protein can be realized.

The term "sample" as used in the assay of the present invention refers to various samples that can contain the cofilin 1 protein and/or a fragment thereof. Examples thereof include cultured cells, a cell homogenate, culture supernatants, and mammalian samples, which contain DNA encoding the cofilin 1 protein or a fragment thereof. The term "mammalian sample" refers to biological samples derived from all mammals, such as tissues collected from mammals (e.g., tissue collected postoperatively), and body fluids such as blood, lymph fluid, urine, spinal fluid, saliva, and seminal fluid. Such a mammalian sample is preferably blood or urine. Examples of blood as used in the present invention include serum, blood plasma, and interstitial fluid. Also, types of mammal are not particularly limited and are preferably primates and more preferably humans.

Specific examples of a peptide region in which an epitope is present include peptide regions consisting of the amino acid sequences shown in SEQ ID NOS: 1 and 2. Of the peptide region consisting of the amino acid sequence shown in SEQ ID NO: 1, a peptide region comprising at least the amino acid sequence shown in SEQ ID NO: 3 is more preferable. Of the peptide region consisting of the amino acid sequence shown in SEQ ID NO: 2, a peptide region comprising at least the amino acid sequence shown in SEQ ID NO: 4 is more preferable. Furthermore, of the peptide region consisting of the amino acid sequence shown in SEQ ID NO: 1, a peptide region comprising at least the amino acid sequences shown in SEQ ID NO: 5 and 6 is furthermore preferable. Of the peptide region consisting of the amino acid sequence shown in SEQ ID NO: 2, a peptide region comprising at least the amino acid sequence shown in SEQ ID NO: 7 is further more preferable. The peptide regions consisting of the amino acid sequences shown in SEQ ID NOS: 5, 6, and 7 are even more preferable as peptide regions in which epitopes are present. This is because epitopes effective for preparation of high-sensitivity antibodies are present in these peptide regions as described above.

Epitopes in the present invention are not particularly limited, as long as they are present on the cofilin 1 protein or a fragment thereof. For example, different epitopes may be present at positions away from each other on the cofilin 1 protein or present at positions close to each other. Furthermore, when each of different epitopes is present in any one of the peptide regions consisting of the amino acid sequences shown in SEQ ID NOS: 1 to 7 above, different epitopes may be present separately on different peptide regions, or present on a single peptide region if the peptide region has a sufficient length of amino acids, so that it can contain multiple epitopes. When epitopes are present on different peptide regions, combinations of peptide regions are not particularly limited. For example, epitopes may be separately present in the peptide regions consisting of the amino acid sequences shown in SEQ ID NOS: 1 and 2, respectively. Alternatively, epitopes may be present separately in the peptide regions consisting of the amino acid sequences shown in SEQ ID NOS: 5 and 6 on the peptide region consisting of the amino acid sequence shown in SEQ ID NO: 1. Alternatively, epitopes may be separately present in the peptide regions consisting of the amino acid sequences shown in SEQ ID NOS: 5 and 6, SEQ ID NOS: 5 and 7, or SEQ ID NOS: 6 and 7, respectively.

For 2 or more types of anti-cofilin 1 monoclonal antibody and/or fragments thereof to be used in this embodiment, the anti-cofilin 1 monoclonal antibody and/or a fragment thereof described in the above embodiment 1 can be used. Examples thereof include a combination of 2 or more types of anti-cofilin 1 monoclonal antibody and/or fragments thereof selected from antibody clone groups listed in Table 1 below, preferably an antibody clone group containing at least 1E2, 2C4, 2D12, 2F5, 3F11, 3G2, 4F12, 4E12, and 4G10, and more preferably an antibody clone group containing at least 1E2, 2C4, 4F12, and 4E12, or, combinations of at least 4F12 and 1E2, 4F12 and 4E12, 1E2 and 3F11, 1E2 and 4E12, 2C4 and 4E12, 3G2 and 4E12, 4G10 and 4E12, 2D12 and 1E2, 2D12 and 2C4, and 4E12 and 2F5.

Examples of a combination of more preferable 2 or more types of anti-cofilin 1 monoclonal antibody and/or fragments thereof to be used in this embodiment include combinations selected from the group consisting of (1) a combination of an anti-cofilin 1 monoclonal antibody or a fragment thereof, in which, at least, in the light chain, CDR1 comprises the sequence shown in SEQ ID NO: 8, CDR2 comprises the sequence shown in SEQ ID NO: 9, and CDR3 comprises the sequence shown in SEQ ID NO: 10, and in the heavy chain, CDR1 comprises the sequence shown in SEQ ID NO: 11, CDR2 comprises the sequence shown in SEQ ID NO: 12, and CDR3 comprises the sequence shown in SEQ ID NO: 13, (2) a combination of an anti-cofilin 1 monoclonal antibody or a fragment thereof, in which in the light chain, CDR1 comprises the sequence shown in SEQ ID NO: 14, CDR2 comprises the sequence shown in SEQ ID NO: 15, and CDR3 comprises the sequence shown in SEQ ID NO: 16, and in the heavy chain, CDR1 comprises the sequence shown in SEQ ID NO: 17, CDR2 comprises the sequence shown in SEQ ID NO: 18, and CDR3 comprises the sequence shown in SEQ ID NO: 19, (3) a combination of an anti-cofilin 1 monoclonal antibody or a fragment thereof, in which in the light chain, CDR1 comprises the sequence shown in SEQ ID NO: 20, CDR2 comprises the sequence shown in SEQ ID NO: 21, and CDR3 comprises the sequence shown in SEQ ID NO: 22, and in the heavy chain, CDR1 comprises the sequence shown in SEQ ID NO: 23, CDR2 comprises the sequence shown in SEQ ID NO: 24, and CDR3 comprises the sequence shown in SEQ ID NO: 25, and (4) a combination of an anti-cofilin 1 monoclonal antibody or a fragment thereof, in which in the light chain, CDR1 comprises the sequence shown in SEQ ID NO: 26, CDR2 comprises the sequence shown in SEQ ID NO: 27, and CDR3 comprises the sequence shown in SEQ ID NO: 28, and in the heavy chain, CDR1 comprises the sequence shown in SEQ ID NO: 29, CDR2 comprises the sequence shown in SEQ ID NO: 30, and CDR3 comprises the sequence shown in SEQ ID NO: 31.

Examples of a combination of further preferable 2 or more types of anti-cofilin 1 monoclonal antibody and/or fragments thereof to be used in this embodiment include (1) a combination of an antibody or a fragment thereof, in which, at least, in the light chain, CDR1 consisting of the sequence shown in SEQ ID NO: 8, CDR2 consisting of the sequence shown in SEQ ID NO: 9, and CDR3 consisting of the sequence shown in SEQ ID NO: 10, and in the heavy chain, CDR1 consisting of the sequence shown in SEQ ID NO: 11, CDR2 consisting of the sequence shown in SEQ ID NO: 12, and CDR3 consisting of the sequence shown in SEQ ID NO: 13, with an antibody or a fragment thereof, in which, in the light chain, CDR1 consisting of the sequence shown in SEQ ID NO: 26, CDR2 consisting of the sequence shown in SEQ ID NO: 27, and CDR3 consisting of the sequence shown in SEQ ID NO: 28, and in the heavy chain, CDR1 consisting of the sequence shown in SEQ ID NO: 29, CDR2 consisting of the sequence shown in SEQ ID NO: 30, and CDR3 consisting of the sequence shown in SEQ ID NO: 31, (2) a combination of an antibody or a fragment thereof, in which, at least, in the light chain, CDR1 consisting of the sequence shown in SEQ ID NO: 8, CDR2 consisting of the sequence shown in SEQ ID NO: 9, and CDR3 consisting of the sequence shown in SEQ ID NO: 10, and in the heavy chain, CDR1 consisting of the sequence shown in SEQ ID NO: 11, CDR2 consisting of the sequence shown in SEQ ID NO: 12, and CDR3 consisting of the sequence shown in SEQ ID NO: 13, with an antibody or a fragment thereof, in which, in the light chain, CDR1 consisting of the sequence shown in SEQ ID NO: 20, CDR2 consisting of the sequence shown in SEQ ID NO: 21, and CDR3 consisting of the sequence shown in SEQ ID NO: 22, and in the heavy chain, CDR1 consisting of the sequence shown in SEQ ID NO: 23, CDR2 consisting of the sequence shown in SEQ ID NO: 24, and CDR3 consisting of the sequence shown in SEQ ID NO: 25, (3) a combination of an antibody or a fragment thereof, in which, at least, in the light chain, CDR1 consisting of the sequence shown in SEQ ID NO: 14, CDR2 consisting of the sequence shown in SEQ ID NO: 15, and CDR3 consisting of the sequence shown in SEQ ID NO: 16, and in the heavy chain, CDR1 consisting of the sequence shown in SEQ ID NO: 17, CDR2 consisting of the sequence shown in SEQ ID NO: 18, and CDR3 consisting of the sequence shown in SEQ ID NO: 19, with an antibody or a fragment thereof, in which, in the light chain, CDR1 consisting of the sequence shown in SEQ ID NO: 20, CDR2 consisting of the sequence shown in SEQ ID NO: 21, and CDR3 consisting of the sequence shown in SEQ ID NO: 22, and in the heavy chain, CDR1 consisting of the sequence shown in SEQ ID NO: 23, CDR2 consisting of the sequence shown in SEQ ID NO: 24, and CDR3 consisting of the sequence shown in SEQ ID NO: 25, and (4) a combination of an antibody or a fragment thereof, in which, at least, in the light chain, CDR1 consisting of the sequence shown in SEQ ID NO: 20, CDR2 consisting of the sequence shown in SEQ ID NO: 21, and CDR3 consisting of the sequence shown in SEQ ID NO: 22, and in the heavy chain, CDR1 consisting of the sequence shown in SEQ ID NO: 23, CDR2 consisting of the sequence shown in SEQ ID NO: 24, and CDR3 consisting of the sequence shown in SEQ ID NO: 25, with an antibody or a fragment thereof, in which, in the light chain, CDR1 consisting of the sequence shown in SEQ ID NO: 26, CDR2 consisting of the sequence shown in SEQ ID NO: 27, and CDR3 consisting of the sequence shown in SEQ ID NO: 28, and in the heavy chain, CDR1 consisting of the sequence shown in SEQ ID NO: 29, CDR2 consisting of the sequence shown in SEQ ID NO: 30, and CDR3 consisting of the sequence shown in SEQ ID NO: 31.

The amino acid sequences shown in SEQ ID NOS: 1 to 7 that are partial sequences of the amino acid sequence constituting the cofilin 1 protein show 100% homology in humans, mice, rats, cattle, dogs and chimpanzees, since the amino acid sequences correspond to regions highly conserved among mammals. The use of antibodies recognizing these sequences makes it possible to construct a versatile cofilin 1 protein measurement system accommodating samples from various mammalian species.

The immunoassay of the present invention can make use of a known immunoassay using 2 or more types of antibody and/or fragments thereof. For example, the immunoassay can be carried out by an immunoassay using a labeled antibody, such as an ELISA method, an EIA method, a fluorescence immunoassay, a radioimmunoassay, or a luminescence immunoassay, a surface plasmon resonance method (SPR method), or a quarts crystal microbalance measurement method (QCM method). Moreover, the immunoassay of the present invention can be achieved using a visually method or by an optical method by mesuring the transmitted light or the scattered light, resulting from the generation of immune complex agglutinates as a result of immunonephelometry, latex agglutination reaction, latex turbidimetry, hemagglutination reaction, particle agglutination reaction, or the like.

The ELISA (Enzyme-Linked ImmunoSorbent Assay) method is also referred to as "enzyme immunosorbent analysis method" and is a method for quantifying a target antigen by detecting the target antigen contained in a trace amount in a sample based on color optical density or fluorescence intensity resulting from an antigen-antibody reaction using an enzyme-labeled antibody or antigen and the action of the enzyme. Specifically, the antibody or a fragment thereof of the present invention or the cofilin 1 protein or a fragment thereof is immobilized on a solid-phase support, and then an immunological reaction between the antibody or the like and the cofilin 1 protein or the like is enzymatically detected. Methods such as a direct method, an indirect method, and a sandwich method are known. In the present invention, particularly the sandwich method is preferably applied. The sandwich method involves binding a 1" antibody (immobilized antibody) immobilized on a solid-phase support to an antigen, adding a $2^{nd}$ antibody (labeled antibody/primary antibody) recognizing an epitope differing from that of the 1" antibody so as to bind it to the antigen, and then detecting the label when the $2^{nd}$ antibody is a labeled antibody, or detecting using a tertiary antibody (secondary antibody) when the $2^{nd}$ antibody is a primary antibody. For detailed information on measurement methods for the ELISA method, see known methods (Ed., Japanese Society of Laboratory Medicine "Clinical Pathology, Extra Edition, Vol. 53, Immunoassay for Clinical Examination-Techniques and Applications-," The Clinical $3^{rd}$ Pathology Press, 1983, Ed., Eiji Ishikawa, "Enzyme Immunoassay," edition, Igaku-Shoin Ltd., 1987, Ed., Tsunehiro Kitagawa et al., "Protein Nucleic Acid Enzyme, Separate Volume No. 31, Enzyme Immunoassay," KYORITSU SHUPPAN CO., LTD, 1987, Ed., Minoru Irie "Radioimmunoassay," Kodansha Scientific Ltd., 1974, Ed., Minoru Irie "Radioimmunoassay 2," Kodansha Scientific Ltd., 1979).

As the above solid-phase support, an insoluble carrier (support) in the form of beads, microplates, test tubes, sticks, test species, or the like can be used, which is made of material such as polystyrene, polycarbonate, polyvinyl toluene, polypropylene, polyethylene, polyvinyl chloride, nylon, polymethacrylate, latex, gelatin, agarose, cellulose, sepharose, glass, metal, ceramics, or magnetic material. The antibody or a fragment thereof of the present invention or the cofilin 1 protein or a fragment thereof can be immobilized onto a solid-phase support by binding it to a support by a known method such as a physical adsorption method, a chemical binding method, or a method using the methods in combination.

As the above labeling substances, in the case of the ELISA method, for example, peroxidase (POD), alkaline phosphatase, β-galactosidase, urease, catalase, glucose oxidase, lactate dehydrogenase, amylase, a biotin-avidin complex, or the like; in the case of fluorescence immunoassay, fluorescein isothiocyanate, tetramethylrho damine isothiocyanate, substituted rhodamine isothiocyanate, dichlorotriazine isothiocyanate, Alexa480, AlexaFluor488, or the like; and in the case of radioimmunoassay, tritium ($^3$H), iodine 125($^{125}$I), iodine 131($^{131}$I), or the like; can be used, but are not limited thereto. Furthermore, in the case of luminescence immunoassay, an NADH-FMNH$_2$-luciferase system, a luminol-hydrogen peroxide-POD system, an acridinium ester system, a dioxetane compound system, or the like can be used. As a method for binding a labeling substance to an antibody, in the case of the ELISA method, a known method such as a glutaraldehyde method, a maleimide method, a pyridyl disulfide method, or a periodic acid method can be used; and in the case of radioimmunoassay, a known method such as a chloramine T method or Bolton-Hunter method can be used.

A case, in which the immunoassay of the present invention is carried out by a sandwich ELISA method using anti-cofilin 1 protein monoclonal antibodies specifically and differently recognizing epitopes that are present in the peptide regions consisting of the amino acid sequences shown in SEQ ID NOS: 5 and 6, is specifically described as an example. However, the embodiments of the present invention are not limited thereto.

First, a monoclonal antibody specifically recognizing an epitope that is present in the peptide region consisting of the amino acid sequence shown in SEQ ID NO: 5 is immobilized on an insoluble support. Antibodies to be immobilized (immobilized antibodies) may be of one type or of several types. Next, a sample containing the cofilin 1 protein is caused to act on the surface of an immobilized antibody, and then an antigen-antibody complex consisting of the immobilized antibody and the cofilin 1 protein is formed on the surface of the solid-phase support. Subsequently, the support is sufficiently washed with a wash solution, so as to remove substances unbound to the immobilized antibodies. Subsequently, labeling is performed using a monoclonal antibody specifically recognizing an epitope that is present in the peptide region consisting of the amino acid sequence shown in SEQ ID NO: 6 to obtain a labeled antibody. The labeled antibody is caused to act on the support to which the complex of the immobilized antibody and the cofilin 1 protein has been bound. The immobilized antibody and the labeled antibody recognize different epitopes of the cofilin 1 protein, respectively, so that on the solid-phase support, a ternary complex consisting of immobilized antibody/cofilin 1 protein/labeled antibody is formed. After unbound labeled antibodies are sufficiently washed off with a wash solution, the cofilin 1 protein existing in the sample can be detected and quantified through detection of the label of the labeled antibody of the ternary complex. The labeled antibodies may be of 1 type or several types. Preferably 2 or more types of labeled antibody are used and 3 types of labeled antibody are more preferably used. Also, when animal species from which an immobilized antibody is derived differs from the animal species from which a labeled antibody is derived, an unlabeled antibody is caused as a primary antibody without labeling to act on an immobilized antibody/cofilin 1 protein complex, and then detection can also be carried out using a labeled secondary antibody that recognizes the primary antibody. In addition, an antibody used for immobilization and an antibody used for labeling can also be used vice versa.

Furthermore, a sample containing a labeled antibody and the cofilin 1 protein is mixed in advance to cause them to form an antigen-antibody complex, and then the complex can be caused to act on an immobilized antibody. When an antibody to be immobilized is biotin-labeled in advance, a sample containing a biotinylated and immobilized antibody and the cofilin 1 protein is mixed with an antibody labeled with a label other than biotin to form an antigen-antibody complex. When the complex is caused to act on a support onto which avidin has been immobilized, the antigen-antibody complex can be detected using labeling other than biotinylation.

Furthermore, in the immunoassay of the present invention, immunochromatographic test strips can also be used. An immunochromatographic test strip is composed of, for example, a sample reservoir made of a material that can easily absorbs a sample, a reagent part containing a diagnostic agent of the present invention, a development part where the reaction product of the sample and the diagnostic agent is developed, a labeling part where the reaction product that has been developed is colored, and a display part where the colored reaction product is developed. Commercially available pregnancy diagnostic agents have forms similar thereto. The principle of the immunoassay is as described below. First, a sample is added to the sample reservoir, the sample reservoir absorbs the sample to cause it to reach the reagent part. Subsequently, an antigen-antibody reaction of the cofilin 1 protein in the sample and the above anti-cofilin 1 partial sequence monoclonal antibody or a fragment thereof takes place at the reagent part, and then the reaction complex migrates in the development part to reach the labeling part. At the labeling part, the above reaction complex reacts with the labeled secondary antibody. When the reaction product from the reaction with the labeled secondary antibody is developed to reach the display part, color development is observed. The above test strip for immunochromatography has extremely low invasiveness, providing no distress and no risk caused by the use of reagents to users. Hence, the test strip can be used for monitoring at home, making it possible to review the results and perform treatment (e.g., surgical resection) at the medical institution level. In such a manner, the results can be led to prevent metastasis and relapse. In addition, the test strip can be currently produced inexpensively in large quantities by a production method as described in JP Patent Publication (Kokai) No. H10-54830 A (1998), for example.

Immunoassay using immunochromatographic test strips is as specifically described below with reference to an example wherein a monoclonal antibody (referred to as "1st antibody") specifically recognizing an epitope that is present in the peptide region consisting of the amino acid sequence shown in SEQ ID NO: 5 and a monoclonal antibody (referred to as "$2^{nd}$ antibody") specifically recognizing an epitope that is present in the peptide region consisting of the amino acid sequence shown in SEQ ID NO: 6 are used. First, a sample containing the cofilin 1 protein is brought into contact with a sample reservoir, and then the sample reservoir absorbs the sample to cause it to reach a reagent part. Subsequently, at the reagent part, an antigen-antibody reaction takes place between the cofilin 1 protein in the sample and the 1st antibody, and then the thus formed antigen-antibody complex migrates through a development part so as to reach a labeling part. At the labeling part, a reaction takes place between the above antigen-antibody complex and the labeled $2^{nd}$ antibody, the reaction product resulting from the reaction with the labeled $2^{nd}$ antibody is developed to reach a display part, and thus color development is observed.

In the assay of the present invention, a surface plasmon resonance method (SPR method) can also be used. The surface plasmon resonance phenomenon refers to a phenomenon in which reflected light intensity is significantly attenuated when a thin metal film is irradiated with a laser beam at a specific angle of incidence (resonance angle). Adsorbates on the surface of the thin metal film can be measured with high sensitivity using an SPR sensor using the principle of the SPR phenomenon. Therefore, an antibody and/or a target antigen is immobilized in advance on the surface of the thin metal film, a sample is caused to pass over the surface of the thin metal film, and thus differences in measured (before and after the passage of the sample) values of adsorbates on the surface of the thin metal film resulting from an antigen-antibody reaction can be detected. A substitution method, an indirect competitive method, and the like are known and any of these methods may be used herein. This technique is known in the art. See Kazuhiro Nagata and Hiroshi Handa, Experimental Methods for Realtime Analysis of Biomaterial Interaction, Springer-Verlag Tokyo, Tokyo, 2000, for example.

Moreover, a quartz crystal microbalance measurement method (QCM method) can also be used for the assay of the present invention. This method uses a phenomenon such that when a substance is adsorbed to the surface of an electrode installed in a quartz resonator, the resonance frequency of the quartz resonator decreases in accordance with the mass. A QCM sensor using the method is a mass measuring sensor capable of quantitatively capturing very small quantities of an adsorbate based on changes in water resonance frequency. This technique is known in the art. For example, see J. Christopher Love, L. A. Estroff, J. K. Kriebel, R. G. Nuzzo, G. M. Whitesides, 2005, Self-Assembled Monolayers of a Form of Nanotechnology, Chemical Review, 105: 1103-1169; Toyosaka Moriizumi, Takamichi Nakamoto, 1997, Sensor Engineering, Shokodo Co., Ltd.

3. Method for Determining Whether or not Gastrointestinal Cancer is Developing

The $3^{rd}$ embodiment of the present invention relates to a method for determining whether or not gastrointestinal cancer is developing. The determination method of the embodiment is characterized by measuring the amount of the cofilin 1 protein and/or a fragment thereof in a sample as a marker for detecting gastrointestinal cancer, and then determining the presence or the absence of gastrointestinal cancer in a subject based on the ratio of the amount of the cofilin 1 protein and/or a fragment thereof in the subject to the amount of the same in a healthy subject. The method of the embodiment comprises a measurement step (1) and a determination step (2). Each step is as specifically described below.

(1) Measurement Step

The term "measurement step" refers to a step for measuring the amount of the cofilin 1 protein in a sample from a subject and the same in a sample from a healthy subject using the assay described in the $2^{nd}$ embodiment above.

The term "subject" refers to an individual subject to be subjected to the determination method of the present invention. Subject types are not particularly limited, as long as the subjects are mammals. Preferably, a subject is a human (hereinafter, when a subject is a human, the subject is referred to as "subject" in the Description).

The term "healthy subject" refers to an individual not affected by at least gastrointestinal cancer, and preferably refers to a healthy individual subject. Such a healthy subject is required to be of the same biological species as that of a subject. For example, in the case of a subject, a healthy subject must also be a human (in the Description, in this case, hereinafter referred to as "healthy subject"). The physical conditions of a healthy subject are preferably the same as or analogous to those of a subject. Physical conditions involve, for example, in the case of a human, race, gender, age, height, body weight, and the like.

Samples to be used in the embodiment are mammalian samples since the samples are derived from subjects or healthy subjects. Specifically, examples of such samples include all biological samples derived from mammals, such as tissue collected from a mammal (e.g., samples collected postoperatively), and body fluids (e.g., blood, lymph fluid, urine, spinal fluid, saliva, and seminal fluid). A sample to be used herein is preferably blood, and is particularly preferably serum or blood plasma. Since measured values must be compared, the types of samples from a subject and a healthy subject must be the same in principle. For example, when a sample from a subject is serum, a sample from a healthy subject is also desired to be serum in principle.

A method for measuring the cofilin 1 protein in a sample may be carried out according to the assay of the $2^{nd}$ embodiment, but the explanation for the detailed information thereof is omitted.

(2) Determination Step

The term "determination step" refers to a step that involves comparing the amount of the cofilin 1 protein and/or a fragment thereof in a sample from a subject with the amount of the same in a sample from a healthy subject as measured by the above measurement step, and then determining that the subject is affected by gastrointestinal cancer when the amount of the cofilin 1 protein and/or a fragment of the subject is significantly statistically higher than that of the healthy subject. The term "gastrointestinal cancer" refers to a primary malignant tumor that is developed in a digestive system organ. Examples of gastrointestinal cancer include esophageal cancer, gastric cancer, duodenal cancer, small intestine carcinoma (including jejunal cancer and ileum cancer), large-bowel cancer (including cancer of cecum, cancer of the colon, and rectal cancer), and cancer of pancreas. Gastrointestinal cancer that is particularly preferable as an object to be determined by the embodiment is gastric cancer. However, an example thereof is not limited to gastrointestinal cancer, cancer to be determined herein may also be an epithelial tumor such as breast cancer, liver cancer, and lung cancer, or skin cancer such as malignant melanomas.

In this step, the amount of the cofilin 1 protein and/or a fragment thereof obtained by the above measurement step from a sample of a subject is compared herein with the amount of the same from a sample of a healthy subject. The amounts to be compared may be relative amounts such as concentrations, or absolute quantities. In the case of absolute quantity, the amounts of samples subjected to measurement should be adjusted in advance to be equivalent to each other between a subject and a healthy subject, or should be converted so that the amounts are equivalent to each other based on the ratio of the amount of the sample from the subject to the amount of the sample from the healthy subject (which are subjected to measurement). In this step, based on the result such that the amount of the cofilin 1 protein and/or a fragment thereof in a sample from a subject is statistically significantly higher or less than that from a healthy subject, a subject exhibiting the amount of the cofilin 1 protein and/or a fragment thereof significantly higher than the other is classified into a group of subjects affected by gastrointestinal cancer; or a subject exhibiting no significant difference is classified into a group not affected by gastrointestinal cancer. A subject classified into such a group of subjects affected by gastrointestinal cancer is determined to have gastrointestinal cancer or determined to highly likely have gastrointestinal cancer. On the other hand, a subject classified into a group of subjects not affected by gastrointestinal cancer is determined to unlikely have gastrointestinal cancer, although the possibility of having gastrointestinal cancer cannot be completely eliminated.

Here, the term "statistically significantly" means that, for example, the significance level of the obtained value is less than 5%, 1%, or 0.1%. Therefore, "statistically significantly high(er)" means that when a quantitative difference in the amount of the cofilin 1 protein and/or a fragment thereof between a subject and a healthy subject is statistically processed, there is a significant difference between the two and the amount of the protein in the subject is higher than that in the healthy subject. In general, cases, in which the amount of the cofilin 1 protein in a blood sample of a subject is 2-fold or more, preferably 3-fold or more, more preferably 4-fold or more, and most preferably 5-fold or more than that of a healthy subject, fall under the above category. If a quantitative difference is 3-fold or more, it can be said that the reliability is high, and the quantitative difference is statistically significantly high. As statistical methods for statistical processing, known statistical methods, by which the presence or the absence of significance can be determined, may be appropriately used, and are not particularly limited. For example, a student's t-test method or multiple comparison procedures can be employed herein.

The amount of the cofilin 1 protein in a blood sample of a healthy subject can be measured every time when the amount of the cofilin 1 protein in a blood sample from a subject is measured, or the amount of the cofilin 1 protein measured in advance can also be used. In particular, the amounts of the cofilin 1 protein of healthy subjects with various physical conditions are measured in advance and then the values are input to a computer to form a database. Through the entry of physical conditions of subjects into the computer, the amount of the cofilin 1 protein of a healthy subject who has physical conditions optimum for comparison with the relevant subject can be used immediately and conveniently.

Gastrointestinal cancer stages to be subjected to the present invention are not particularly limited, ranging from early gastrointestinal cancer to terminal gastrointestinal cancer. In particular, the determination method of the present invention has high sensitivity for the antibody and/or a fragment thereof of the embodiment 1, so that it is excellent in that even gastrointestinal cancer at an early stage, the detection of which has been difficult with conventional methods, can be detected. The term "(early) gastrointestinal cancer at an early stage" refers to gastrointestinal cancer characterized in that it is limited to a spot (intramucosal) where tumor is developed and does not invade the surrounding tissue or the infiltration range is limited locally even if there is the invasion of surrounding tissue. Early detection of gastrointestinal cancer significantly improves the 5-year survival rate, so that the present invention capable of determining the disease at an early stage is practically highly beneficial.

As described above, according to the method of the present invention for determining whether or not gastrointestinal cancer is developing, a marker for detection of gastrointestinal cancer in a blood sample is immunologically assayed using an antibody, so as to be able to conveniently and rapidly determine at an early stage if a subject is affected by gastrointestinal cancer.

The determination method of the present invention makes it possible to determine if a subject is affected by gastrointestinal cancer even at an early stage using a blood plasma sample, a serum sample or the like from the subject.

4. Kit for Cofilin 1 Protein Quantification Using the Assay of the Present Invention The 4th embodiment of the present invention relates to a kit for cofilin 1 protein quantification. The kit of this embodiment is characterized by comprising, as essential components, 2 or more types of anti-cofilin 1 monoclonal antibody and/or fragments thereof specifically recognizing different epitopes on the amino acid sequence constituting the cofilin 1 protein. Examples of the above antibodies and/or fragments thereof contained in this kit include the antibodies and/or fragments thereof described in the embodiment 1 above. Examples of a combination of 2 or more types of antibody and/or fragments thereof contained in the kit include combinations of the antibodies and/or fragments thereof described in the embodiment 2 above. In addition, the kit may further contain a labeled secondary antibody, a substrate required for detection of a label, a positive control or a negative control, a buffer (to be used for dilution or washing of a sample.) and/or instructions, and the like, as necessary.

According to the present invention, the cofilin 1 protein that is contained in an appropriate sample such as blood can be easily and conveniently measured by the immunoassay as described in the 1st embodiment above. Furthermore, based on the result and the method of the $3^{rd}$ embodiment above, the convenient and rapid determination of the presence or the absence of gastrointestinal cancer in a subject from which a sample is obtained becomes possible.

EXAMPLES

The present invention is described more specifically based on the Examples, but the present invention is not limited by these examples.

Example 1

Preparation of Recombinant Cofilin 1 Protein by *Escherichia coli*

(Preparation of Human Cofilin 1 Gene)

For preparation of a recombinant human cofilin 1 protein to be used as an immunogen for an antibody, human cofilin 1 mRNA was prepared from HEK293 cells of a human fetal kidney cell line. mRNA was specifically prepared using a Qia shredder and an RNeasy mini kit (Qiagen) in accordance with the protocols included therewith.

Next, cDNA was synthesized using reverse transcriptase SuperscriptII (Invitrogen) and the aforementioned obtained total mRNA as a template, and then a human cDNA library was constructed. A reverse transcription reaction was conducted in accordance with the protocols included with the enzyme.

Subsequently, PCR was carried out using the thus obtained human cDNA library as a template and a primer set consisting of the nucleotide sequences shown in SEQ ID NOS: 32 and 35. The nucleotide sequence shown in SEQ ID NO: 32 contains a portion of the 5' terminal region of the human cofilin 1 gene and a BamH I recognition sequence upstream of such portion. The nucleotide sequence shown in SEQ ID NO: 35 contains a portion of the 3' terminal region of the human cofilin 1 gene and an EcoR I recognition sequence downstream of the portion. A PCR solution was prepared using KOD (Toyobo Co., Ltd.) as DNA polymerase, so that it contained 10 ng of a cDNA library and 10 pmol of each primer in accordance with the protocols included with KOD. Reaction conditions are as follows. PCR was carried out by repeating 35 times a cycle consisting of, after 5 minutes of heating at a temperature of 94° C. and keeping the temperature at 94° C. for 15 seconds, 55° C. for 30 seconds, and 68° C. for 30 seconds, followed by keeping the final temperature at 68° C. for 4 minutes. The thus amplified DNA fragment was purified using Wizard SV Gel and PCR Clean-up System (Promega). A PCR product with a full length of about 500 bp was obtained by the reaction.

The obtained DNA fragment was cleaved with BamH I and EcoR I, and then a ligation reaction was conducted to incorporate the resultant into open circular pET30a (Novagen) that had been subjected to cleavage with BamH I and EcoR I, and treatment with BAP. Ligation High (Toyobo Co., Ltd.) was used as DNA ligase, and then the reaction was conducted in accordance with the protocols included therewith. Subsequently, competent cells were transformed using a solution after the ligation reaction. Competent cells were specifically prepared using a DH5a *Escherichia coli* strain (Takara Bio Inc.) in accordance with the protocols included therewith. Transformed cells were applied onto an LB plate containing antibiotic kanamycin (100 μg/mL), and then cultured at 37° C. overnight. The thus obtained transformant was cultured in an LB liquid medium containing 100 μg/mL kanamycin at 37° C. overnight, and thus pET30a_cofilin 1 of interest was obtained by Mini-Prep.

Subsequently, PCR was carried out using the obtained pET30a_cofilin 1 gene (10 ng) as a template and a primer set consisting of the nucleotide sequences shown in SEQ ID NOS: 39 and 40. The nucleotide sequence shown in SEQ ID NO: 39 contained a portion of the 5' terminal region of the human cofilin 1 gene and an EcoR I recognition sequence upstream of the portion. The nucleotide sequence shown in SEQ ID NO: 40 contained a portion of the 3' terminal region of the human cofilin 1 gene and a Bgl II recognition sequence downstream of the portion. A PCR solution was prepared using KOD (Toyobo Co., Ltd.) as DNA polymerase in accordance with the protocols included with KOD, so that it contained 10 ng of the cDNA library and 10 pmol of each primer. Reaction conditions are as follows. PCR was carried out by repeating 35 times a cycle consisting of, after 5 minutes of heating at a temperature of 94° C. and keeping the temperature at 94° C. for 15 seconds, 55° C. for 30 seconds, and 68° C. for 30 seconds, followed by keeping the final temperature at 68° C. for 4 minutes. The thus amplified DNA fragment was purified using Wizard SV Gel and PCR Clean-up System (Promega). A PCR product with a full length of about 500 bp was obtained by the reaction.

The obtained DNA fragment was cleaved with EcoR I and Bgl II, and then a ligation reaction was conducted to incorporate the resultant into open circular pCMV-Myc (Clontech) that had been subjected to cleavage with EcoR I and BamH I, and treatment with BAP. Ligation High (Toyobo Co., Ltd.) was used as DNA ligase, and then the reaction was conducted in accordance with the protocols included therewith. Subsequently, competent cells were transformed using a solution after the ligation reaction. Competent cells were specifically prepared using a DH5α. *Escherichia coli* strain (Takara Bio Inc.) in accordance with the protocols included therewith. Transformed cells were applied onto an LB plate containing antibiotic kanamycin (50 μg/mL), and then cultured at 37° C. overnight. The thus obtained transformant was cultured in an LB liquid medium containing 100 μg/mL ampicillin at 37° C. overnight, and thus pCMV-Myc_human cofilin 1 of interest was obtained by Mini-Prep.

(Preparation of Recombinant Human Cofilin 1 Protein)

For preparation of a recombinant human cofilin 1 protein, Rosetta-Gami 2 *Escherichia coli* strain (Novagen) was transformed with pET30a_cofilin 1. The obtained transformant was pre-cultured in 10 mL of an LB medium containing kanamycin and chloramphenicol at 37° C. overnight. Next, the pre-cultured product was seeded in 1 L of the same medium and then cultured at 37° C. for 5 hours. IPTG with a final concentration of 0.25 mM was added, cells were cultured at 32° C. for 12 hours, to induce the expression of the recombinant human cofilin 1 protein of interest, and then centrifugation was performed to collect microorganisms.

The obtained microorganisms were washed with PBS, and then an insoluble fraction was prepared as a precipitate using B-PER (PIERCE). The procedure was specifically performed in accordance with the protocols included therewith. Next, the insoluble fraction was solubilized with 6 M urea, and then a histidine-tagged human cofilin 1 protein was adsorbed to TALON Metal Affinity Resin (CLONETECH). The protein-adsorbed resin was washed with 6 M urea containing 10 mM imidazole, and then eluted using a 6 M urea solution containing 1 M imidazole.

Next, from the obtained elution fraction, protein refolding was carried out. First, the fraction was dialyzed overnight against a PBS solution supplemented with 6 M urea, PBS was gradually added to the dialysis solution until the final concentration of urea in the dialysis solution reached 1 M for dilution. Finally, the resultant was dialyzed against a newly prepared PBS solution overnight. The obtained refolding solution was subjected to acrylamide gel electrophoresis. Purification of a histidine tagged human cofilin 1 protein having a molecular weight of about 16,000 Da was confirmed by Coomassie brilliant blue staining.

Example 2

Preparation and Selection of Mouse Monoclonal Antibody Against Human Cofilin 1 Protein (Production of Anti-Human Cofilin 1 Antibody-Producing Mouse)

50 μL of a 1 mg/mL human cofilin 1 protein solution obtained in Example 1 was mixed with 50 μL of a Sigma adjuvant system (Sigma). The total amount of the solution was intraperitoneally administered to a 6-week-old BALB/c mouse. After 2 weeks and 4 weeks, similarly prepared human cofilin 1 protein solution was administered in the same volume. Subsequently, 100 μL of blood was collected via mouse tail vein. The sample was left to stand overnight and then centrifuged at 5000×g for 5 minutes, and thus the supernatant was collected as serum.

100 μL of the 0.1 μg/mL human cofilin 1 protein solution was added to each well of a flat bottom 96-well plate (Nunc), followed by overnight immobilization. After the protein solution in each well was discarded, 400 μL of a blocking solution diluted 4-fold (PBS-T containing 1% BSA) was poured thereinto and then the plate was left to stand for 1 hour at room temperature. Subsequently, the plate was washed with PBS-T so as to prepare a plate to which the human cofilin 1 protein had been immobilized. A serum sample obtained above was diluted 1000-fold, 100 μL of the solution was added to each well of the plate to which the human cofilin 1 protein had been immobilized, and then the plate was left to stand at room temperature for 1 hour. Subsequently, solutions within wells were discarded, the plate was washed with PBS-T, 100 μL of an HRP-labeled anti-mouse IgG solution (GE Healthcare) was added, and then the plate was further left to stand at room temperature for 1 hour. Solutions within wells were discarded, the plate was washed with PBS-T, and then 100 μL of a TMB solution was added for 15 minutes of reaction. Color development resulting from the reaction was confirmed with absorbance at 450 nm. It was determined that an antibody against the human cofilin 1 protein was produced in mice from which blood samples with colors developed had been collected.

(Preparation of Anti-Human Cofilin 1 Monoclonal Antibody)

A human cofilin 1 protein solution prepared in a manner similar to the above was intraperitoneally administered to a mouse for which antibody production against the human cofilin 1 protein had been confirmed. 3 days later, splenectomy was carried out. The excised spleen was punctured with a syringe, and then an RPMI1640 medium (GIBCO) was injected to extrude spleen cells, so that a spleen cell solution was obtained. The obtained spleen cell solution was centrifuged at 1200 rpm for 7 minutes, to remove a supernatant, and then the resultant was washed with an RPMI1640 medium. The resultant was suspended again in an RPMI1640 medium, the number of cells was counted, and thus a SP2/0 myeloma cell solution containing SP2/0 myeloma cells in number 1/10 the number of spleen cells was prepared. Both cell solutions were mixed, and the mixture was centrifuged at 2200 rpm for 10 minutes, following which the supernatant was discarded. Cells were loosened by tapping, 1 mL of a solution prepared by mixing PEG (ROCHE) with HBSS (GIBCO) at a ratio of 5:1 was added to the cells, and then the solution was stirred. In the following procedures, solutions or media used herein were all maintained at 37° C. and then used, unless particularly specified.

An RPMI1640 medium (9 mL) was gradually added to the cell solution supplemented with PEG and HBSS for 5 minutes. The solution was slowly mixed, centrifuged at 2200 rpm for 10 minutes, and thus the supernatant was removed. The obtained precipitated cells were suspended in an RPMI1640 medium supplemented with 15% FCS and HAT (ROCHE). The suspension was added to a 96-well cell culture plate (Greiner Bio-One) at 200 µL per well, followed by 1 week of culture at 37° C. under 5% $CO_2$.

Colonies that had grown under conditions in which HAT had been added thereto were determined to be colonies of hybridomas resulting from the fusion of spleen cells to myeloma cells. The supernatant of each well in which the colonies had grown was diluted 5-fold, and then 100 µL of the solution was added to each well of the plate to which the human cofilin 1 protein had been immobilized, and then whether or not antibody production was taking place was determined by a method similar to the above. Wells for which antibody production had been confirmed were designated as being positive. Colonies in positive wells were suspended in an RPMI medium containing 15% FCS and HT (Invitrogen), and then cloning of positive clones was carried out by limiting dilution. 39 types of hybridoma obtained as a result of cloning were conditioned to an SFM medium, and then antibody production was carried out. Hybridomas were seeded into a 100% SFM medium (60 mL) at 1×10⁵ cells/mL and then cultured for 10 days until all cells had died. Then the culture solution was centrifuged at 3000 rpm for 15 minutes to remove the cells. Antibodies contained in the obtained culture supernatants were purified using ProSep-vA Ultra chromatography (Millipore).

Example 3

Epitope Mapping of Cofilin 1 Protein Antibody (Preparation of Deletion Mutant)

The thus obtained 39 types of purified antibody were subjected to epitope sequencing by the following techniques. First, 5 types of human cofilin 1 protein deletion mutant (mutant A to mutant E) in Example 1 and the full-length human cofilin 1 protein as GST fusion proteins were prepared (FIG. 1).

PCR was carried out for mutant A using pET30a_cofilin 1 gene (10 ng) as a template and a primer set consisting of the nucleotide sequences shown in SEQ ID NOS: 32 and 37, for mutant B using the same template and a primer set consisting of the nucleotide sequences shown in SEQ ID NOS: 33 and 35, for mutant C using the same template and a primer set consisting of the nucleotide sequences shown in SEQ ID NOS: 32 and 38, for mutant D using the same template and a primer set consisting of the nucleotide sequences shown in SEQ ID NOS: 32 and 36, for mutant E using the same template and a primer set consisting of the nucleotide sequences shown in SEQ ID NOS: 34 and 38, and for the full-length human cofilin 1 using the same template and a primer set consisting of the nucleotide sequences shown in SEQ ID NOS: 32 and 35, so that each gene was obtained. The nucleotide sequences shown in SEQ ID NOS: 32, 33, and 34 contained a portion of the 5' terminal region of the human cofilin 1 gene and a BamH I recognition sequence upstream of the portion. The nucleotide sequences shown in SEQ ID NOS: 35 to 38 contained a portion of the 3' terminal region of the human cofilin 1 gene and an EcoR I recognition sequence downstream of the portion.

The obtained 6 types of PCR product were each cleaved with BamH I and EcoR I, and then a ligation reaction was conducted to incorporate the resultant into open circular pGEX6P-1 (GE Healthcare) that had been subjected to cleavage with BamH I and EcoR I, and treatment with BAP. Ligation High (Toyobo Co., Ltd.) was used as DNA ligase, and then the reaction was conducted in accordance with the protocols included therewith. Subsequently, competent cells were transformed using a solution obtained after the ligation reaction. Competent cells were specifically prepared using a DH5α, *Escherichia coli* strain (Takara Bio Inc.) in accordance with the protocols included therewith. Transformed cells were applied onto an LB plate containing antibiotic ampicillin (100 µg/mL), and then cultured at 37° C. overnight. The thus obtained transformant was cultured in an LB liquid medium containing 100 µg/mL ampicillin at 37° C. overnight, and thus 6 types of expression vector constructed by introducing the full-length human cofilin 1 protein of interest and the 5 types of deletion mutant gene were obtained by Mini-Prep.

The above 6 types of expression vector were each transformed into Rosetta-Gami2 *Escherichia coli* strain (Novagen). With procedures described below, recombinant GST fusion proteins of the full-length human cofilin 1 and the 5 types of deletion mutant were prepared. First, the transformant was pre-cultured overnight at 37° C. in 10 mL of an LB medium containing ampicillin and chloramphenicol. Next, the pre-cultured cells were seeded in 1 L of the same medium and then cultured at 37° C. for 5 hours. IPTG having a final concentration of 0.5 mM was added and then the cells were cultured at 37° C. for 12 hours, so as to induce the expression of the recombinant human cofilin 1 protein of interest. Microorganisms were then collected by centrifugation.

The obtained microorganisms were washed with PBS and then a soluble fraction was obtained using B-PER (PIERCE). The procedure was specifically carried out in accordance with the protocols included therewith. Next, the recombinant GST fusion protein in the soluble fraction was adsorbed to glutathione sepharose 4B (GE Healthcare). The resin to which the protein had been adsorbed was washed with TBS (150 mM NaCl, 50 mM Tris-Cl, 5 mM EDTA, pH8.0), and then eluted with TBS containing 10 mM reduced glutathione. The obtained GST fusion protein was adjusted to 1 mg/mL and then the solution was used for the following experiment.

(Evaluation of Reactivity of Monoclonal Antibody to Human Cofilin 1 Deletion Mutant)

A solution (1 µg/mL) of each recombinant GST fusion protein of the full-length human cofilin 1 and 5 types of deletion mutant was prepared. The solution (100 µl each) was poured into each well of a flat bottom 96-well plate (Nunc), followed by 3 hours of immobilization. The GST fusion protein solution within each well was discarded, 400 µL of a blocking solution (PBS-T containing 1% BSA) was poured into each well, and then the plate was left to stand for 1 hour at 4° C. Subsequently, the solution was discarded, the plate was washed with PBS-T, and thus a plate to which an antigen protein had been immobilized was prepared. Also, a blank plate was also prepared by performing only a blocking reaction without performing immobilization of the GST fusion protein. Next, each of the 39 types of anti-human cofilin 1 monoclonal antibody diluted with PBS-T containing 1% BSA to have a final concentration of 1 µg/mL was poured into the blank plate and the plate to which the GST fusion protein had been immobilized, followed by 1 hour of reaction at room temperature. The solution within each well was discarded. The plate was washed with PBS-T, and then 100 µl of an HRP-labeled anti-mouse IgG antibody solution (GE Healthcare) was added for 1 hour of reaction at room temperature. Subsequently, after washing with PBS-T, 100 µL of the TMB solution was added for 1 minute of color reaction. The reaction was stopped by adding 100 μL of a 2 N sulfuric acid solution. Color development was confirmed by measuring absorbance at 450 nm. When the absorbance was higher by 0.5 or more than that of a blank well, "reactivity" was confirmed, suggesting the binding of the immobilized recombinant GST fusion protein to the monoclonal antibody added. The binding of each of the 39 types of anti-human cofilin 1 monoclonal antibody to the GST fusion protein is as shown in Table 1. In Table 1, a result in which "reactivity" was confirmed is indicated with "o" and a result in which "non-reactivity" was confirmed is indicated with "x."

(Identification of Epitope Sequence)

Epitope sequences were determined using as indices differences in reactivity of the 39 types of anti-human cofilin 1 monoclonal antibody to the full-length human cofilin 1 and the 5 types of deletion mutant. For example, the 4E12 antibody reacted to only the full-length human cofilin 1 protein and mutant B but did not react to other deletion mutants. Therefore, at least a partial sequence of the epitope sequence of the 4E12 antibody is present in the full-length human cofilin 1 protein and mutant B, but is contained in the C3 region shown in SEQ ID NO: 4 corresponding to a deleted region in other deletion mutants (FIG. 1).

Similar analysis was conducted for other clones. As a result, the epitopes to be recognized by the 39 types of anti-human cofilin 1 monoclonal antibody were classified by their locations; that is, each epitope was present in any one of the peptide regions (N1, N2, M, C1, C2, and C3) consisting of partial sequences of the human cofilin 1 protein (Table 1).

TABLE 1

| Antibody clone name | Deletion mutant | | | | | Full-length | Epitope |
|---|---|---|---|---|---|---|---|
| | A | B | C | D | E | | |
| 1B10 | o | o | o | o | o | o | M |
| 1D5 | o | o | o | o | x | o | N2 |
| 1D11 | o | o | o | o | o | o | M |
| 1E2 | o | o | x | o | x | o | C1 |
| 2A1 | o | o | o | o | o | o | M |
| 2C11 | x | o | x | o | x | o | C2 |
| 2C12 | o | o | o | o | o | o | M |
| 2D12 | x | o | x | x | x | o | C3 |
| 2E2 | o | o | o | o | x | o | N2 |
| 2F5 | o | o | x | o | x | o | C1 |
| 2F13 | o | o | x | o | x | o | C1 |
| 2C4 | o | o | x | o | x | o | C1 |
| 3B4 | o | o | o | o | o | o | M |
| 3D2 | o | o | o | o | o | o | M |
| 3F11 | x | o | x | x | x | o | C3 |
| 3F12 | o | o | o | o | o | o | M |
| 3G2 | o | o | x | o | x | o | C1 |
| 4B10 | o | o | o | o | o | o | M |
| 4C4 | o | o | x | o | x | o | C1 |
| 4D1 | o | o | o | o | o | o | M |
| 4E12 | x | o | x | x | x | o | C3 |
| 4F12 | o | o | o | o | x | o | N2 |
| 4G1 | o | o | o | o | o | o | M |
| 4G10 | o | o | x | o | x | o | C1 |
| 5A10 | o | o | o | o | o | o | M |
| 5C12 | o | o | o | o | o | o | M |
| 5D12 | o | o | o | o | o | o | M |
| 5E4 | o | o | o | o | x | o | N2 |
| 5E7 | o | o | o | o | o | o | M |
| 5G7 | o | o | o | o | x | o | N2 |
| 6A3 | o | o | o | o | o | o | M |
| 6G6 | o | o | o | o | o | o | M |
| 6A6 | o | o | o | o | x | o | N2 |
| 6B11 | o | o | o | o | x | o | N2 |
| 6C1 | o | o | o | o | o | o | M |
| 6C3 | o | o | o | o | x | o | N2 |

TABLE 1-continued

| Antibody clone name | Deletion mutant | | | | | Full-length | Epitope |
|---|---|---|---|---|---|---|---|
| | A | B | C | D | E | | |
| 6C12 | o | o | o | o | x | o | N2 |
| 6D12 | o | o | o | o | x | o | N2 |
| 6H1 | o | o | o | o | o | o | M |

Reactivity: o
Non-Reactivity: x

Example 4

Construction of ELISA for Measurement of Human Cofilin 1 Protein (Human Cofilin 1 Protein Expression in HEK293 Cells)

Figure 2:
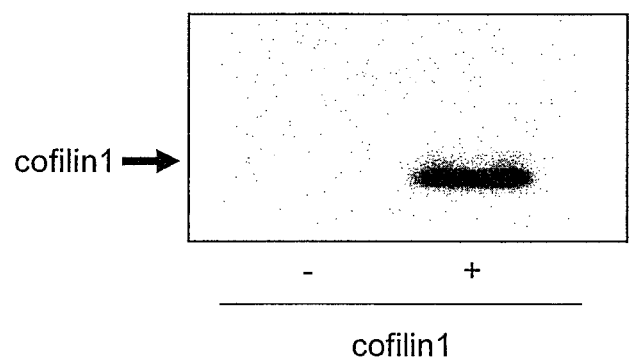
FIG. 2 shows the results of Western blotting performed for a sample of a cell line expressing a human cofilin 1 protein. "+" indicates the result for HEK293 cells in which pCMV-Myc_human cofilin 1 was introduced, and "−" indicates the result for HEK293 cells in which only pCMV-Myc vector was introduced.

HEK293 cells ($2 \times 10^6$ cells) were cultured overnight in DMEM (GIBCO) containing 10% FCS using cell culture dishes (Corning). pCMV-Myc_human cofilin 1 or pCMV-Myc was introduced into the cells using lipofectamine 2000 (Invitrogen) in accordance with the protocols included therewith. After 2 days of culture, the medium was removed. After washing with 10 mL of PBS, 1.0 mL of a 1% NP40 buffer (1% NP40, 150 mM NaCl, 5 mM EDTA, 100 mM Tris-Cl, and pH 8.0) was added, and then cells were left to stand for 30 minutes at 4° C. Cells were suspended in 1% NP40 buffer, and then the solution was transferred to 1-mL centrifugal tubes. After centrifugation at 15,000×g, supernatants were collected. Each sample (5 μL) was denatured with an LDS sample buffer (Invitrogen) and then subjected to electrophoresis using NuPage 4-12% Bis-Tris Gel (Invitrogen). The proteins were transferred to a PVDF membrane. The resultant underwent reaction with a rabbit polyclonal antibody (Proteintech Group), and then with a peroxidase-labeled secondary antibody. Proteins that have immunologically reacted were exposed to X-ray films using Western Lightning Plus-ECL (Perkin Elmer) for visualization. As a result, the band representing the human cofilin 1 protein was detected for only cells into which pCMV-Myc_human cofilin 1 had been introduced (FIG. 2).

(Selection of Antibody Combination)

For selection of a combination of 2 types of antibody for sandwich ELISA, by which high-sensitivity detection is possible, 1521 combinations (39×39 combinations) obtained from the 39 types of antibody and the 39 types of biotin-labeled antibody were compared for superiority and inferiority in detection sensitivity in sandwich ELISA. ELISA was carried out using as a positive control sample, a cell extract into which pCMV-Myc_cofilin 1 had been introduced and using as a negative control, a cell extract into which pCMV-Myc had been introduced. Superiority and inferiority in detection sensitivity were determined using as an index a value found by subtracting the measured value of the negative control from the measured value of the positive control.

Figure 3:
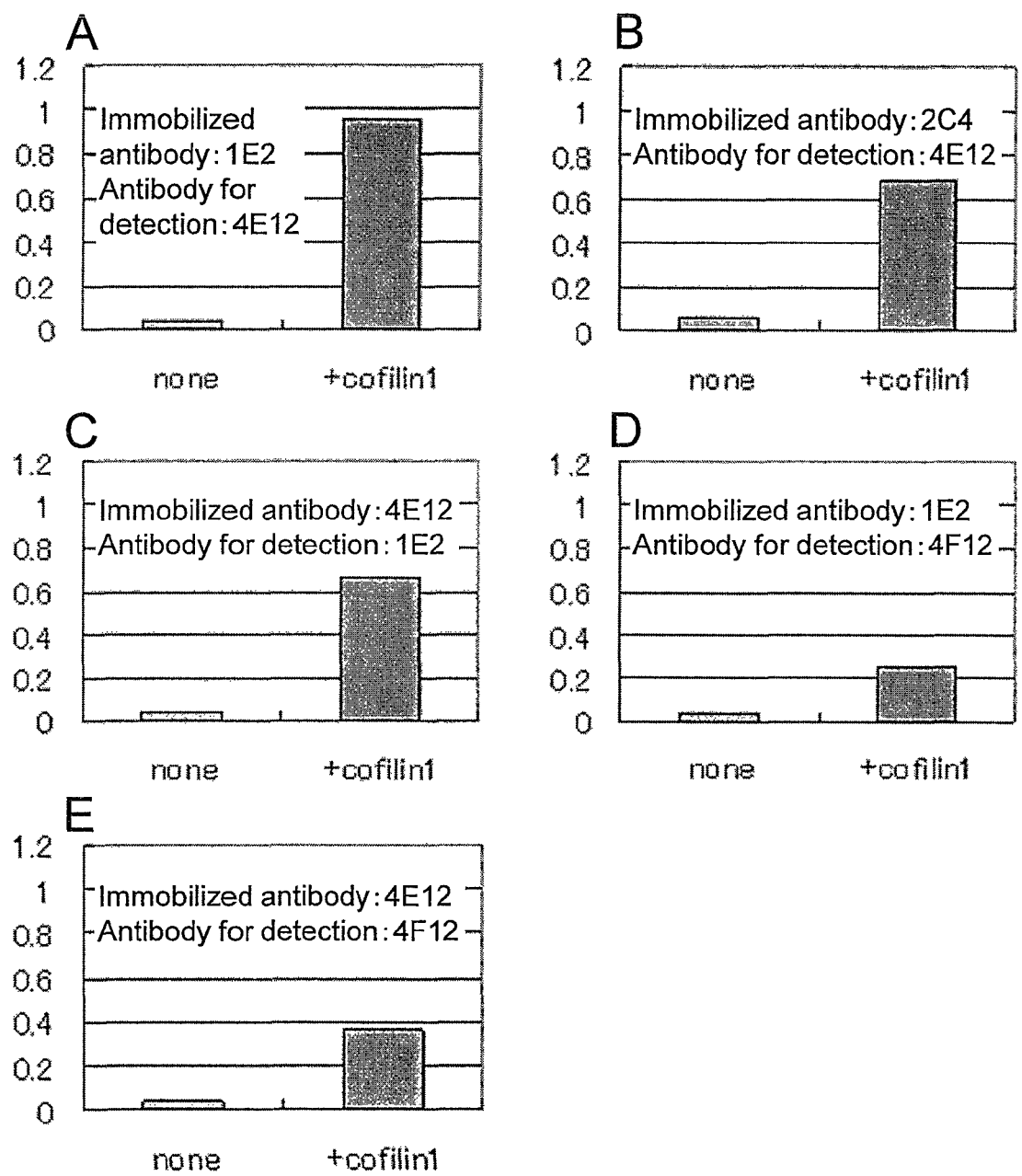
FIGS. 3A-3E show the detection sensitivity for the cofilin 1 protein, as detected by sandwich ELISA using two different types of anti-cofilin 1 monoclonal antibody.

First, a solution (3 pg/mL) of each of the 39 types of purified antibody was prepared. The solution (100 μL each) was added to each well of a flat bottom 96-well plate (Nunc), followed by 5 hours of immobilization. The purified antibody solution within each well was discarded. A blocking solution (400 μL) (PBS-T containing 1% BSA) was poured thereinto and then the plate was left to stand overnight at 4° C. Subsequently, the solution was discarded and then the plate was washed with PBS-T, so that a plate to which the purified antibody had been immobilized was prepared. Next, a protein extract of cells into which pCMV-Myc_human cofilin 1 had been introduced or a protein extract of cells into which pCMV-Myc had been introduced was diluted 10-fold with 1% NP40 buffer. The solution (100 µL) was added to 39 wells per type of immobilized antibody, followed by 1 hour of reaction at room temperature. Subsequently, the solution within each well was discarded, and then the plate was washed with PBS-T. The thus obtained 39 types of biotinylated antibody were diluted with 1% NP40 buffer containing 1% BSA to 0.5 µg/mL. Each diluted solution was added to wells wherein the extract of the pCMV-Myc_human cofilin 1-introduced cells had been reacted and to wells wherein the extract of the pCMV-Myc-introduced cells had been reacted, followed by 1 hour of reaction at room temperature. The solution within each well was discarded and then the plate was washed with PBS-T, followed by 1 hour of reaction with 100 µL of an avidin-HRP solution (R&D) at room temperature. Furthermore, the avidin-HRP solution was discarded, the plate was washed with PBS-T, and then 100 µL of a TMB solution was added for 5 minutes of reaction. The reaction was stopped by adding 100 µL of a 2N sulfuric acid solution. Color development was confirmed by measuring absorbance at 450 nm. For all combinations of the 39 types of immobilized antibody and the 39 types of biotin-labeled antibody, the human cofilin 1 protein concentrations of a positive control and a negative control were measured. Antibody combinations with high sensitivity were determined on the basis of the value found by subtracting the value of a negative control from the value of a positive control. As a result, it was revealed that the human cofilin 1 protein can be detected with particularly high sensitivity with the use of 2 types of anti-cofilin 1 monoclonal antibody specifically recognizing any one of C1 region, C3 region, and N2 region (FIG. 3).

Example 5

Analysis of Amino Acid Sequence of Anti-Cofilin 1 Monoclonal Antibody (Determination of Monoclonal Antibody Light Chain and Heavy Chain cDNA Sequences and the Amino Acid Sequences Using Hybridomas)

For the 4 types of antibody required for the selected 5 types of antibody combination, the cDNA sequences and the amino acid sequences of light chain and heavy chain were determined. First, a hybridoma producing each antibody was cultured using an RPMI1640 medium supplemented with 15% FCS at 37° C. under 5% $CO_2$ to $1 \times 10^6$ cells/mL. Subsequently, the culture solution was centrifuged at 1200 rpm for 5 minutes, thereby collecting cells. From the thus collected hybridomas, mRNA was prepared. mRNA preparation was specifically carried out using a Qia shredder and an RNeazy mini kit (Qiagen) in accordance with the protocols included therewith. Next, cDNA was synthesized using reverse transcriptase SuperscriptII (Invitrogen), the obtained Total mRNA as a template, and oligo dT primers, so that a cDNA library was constructed.

PCR was carried out using the cDNA library obtained for each hybridoma as a template and Mouse Ig Primers (Novagen). The amplification product (mouse immunoglobulin variable region cDNA) was subjected to ligation using a ZERO BLUNT TOPO PCR cloning Kit (Invitrogen). Next, competent cells were transformed with each ligation reaction solution. Competent cells were specifically transformed using DH5a, (Takara Bio Inc.) in accordance with the protocols included therewith. Transformed cells were applied onto an LB plate containing 50 µg/mL kanamycin and then cultured at 37° C. overnight. Four clones each of the transformant derived from each amplification product were seeded in LB liquid medium containing 50 µg/mL kanamycin and then cultured at 37° C. overnight. As a result of preparing a vector DNA solution from each culture solution by Mini-Prep, 4 types each of vector solution (into which DNA encoding the monoclonal antibody had been incorporated) were obtained per amplification product.

For the thus obtained vector solutions, DNA sequence analysis was conducted for regions encoding the monoclonal antibodies using an M13 primer. Analysis was conducted using a 3130×1 genetic analyzer (Applied Biosystems). Clones having no stop codon in insertion regions were determined to have the DNA sequence encoding the Monoclonal antibody of interest. The light chain and heavy chain DNA sequences of the above 4 antibodies (1E2, 2C4, 4E12, 4F12) were determined. For the thus determined DNA sequences, the amino acid sequences encoding the DNA sequences were determined based on the frequency of codon usage of *Escherichia coli*. Thus, the sequences shown in SEQ ID NOS: 8 to 31 could be obtained.

The amino acid sequences shown in SEQ ID NOS: 8 to 31 were obtained as the amino acid sequences encoding 1E2. More specifically, SEQ ID NOS: 8, 9, and 10 encode 1E2 light chain CDR1, CDR2, and CDR3, respectively, and the amino acid sequences shown in SEQ ID NOS: 11, 12, and 13 encode 1E2 heavy chain CDR1, CDR2, and CDR3, respectively.

The amino acid sequences shown in SEQ ID NOS: 14 to 19 were obtained as the amino acid sequences encoding 2C4. More specifically, SEQ ID NOS: 14 to 16 encode 2C4 light chain CDR1 to 3, respectively. Also the amino acid sequences shown in SEQ ID NOS: 17 to 19 encode 2C4 heavy chain CDR1 to 3, respectively.

The amino acid sequences shown in SEQ ID NOS: 20 to 25 were obtained as the amino acid sequences encoding 4E12. More specifically, SEQ ID NOS: 20 to 22 encode 4E12 light chain CDR1 to 3, respectively. The amino acid sequences shown in SEQ ID NOS: 23 to 25 encode 4E12 heavy chain CDR1 to 3, respectively.

The amino acid sequences shown in SEQ ID NOS: 26 to 31 were obtained as the amino acid sequences encoding 4F12. More specifically, SEQ ID NOS: 26 to 28 encode 4F12 light chain CDR1 to 3, respectively. The amino acid sequences shown in SEQ ID NOS: 29 to 31 encode 4F12 heavy chain CDR1 to 3, respectively.

Example 6

Detection of Human Cofilin 1 Protein by Sandwich ELISA Method Using Monoclonal Antibody 1E2 and Monoclonal Antibody 4E12

It was thus revealed in Example 3 that the human cofilin 1 protein can be detected with the highest sensitivity by the sandwich ELISA method using: from among the amino acid sequence shown in SEQ ID NO: 1, the 1E2 monoclonal antibody specifically recognizing at least an epitope that is present in the peptide region consisting of the amino acid sequence shown in SEQ ID NO: 5; and from among the amino acid sequence shown in SEQ ID NO: 1, a biotin-labeled 4E12 monoclonal antibody specifically recognizing at least an epitope that is present in a peptide region consisting of the amino acid sequence shown in SEQ ID NO: 6. Hence, a His-human cofilin 1 protein was serially diluted with TBS buffer containing 1% BSA and 1% NP40 from 1000 ng/mL to 10 pg/mL. Detection sensitivity of the sandwich ELISA was calculated by measurement using the diluted solutions as samples. As a result, the minimum detection limit (the minimum concentration at which the mean value+2SD does not overlap with the mean value of subject−2SD) of the ELISA method using a combination of 1E2 and 4E12 was 10 pg/mL (FIG. 4 (indicated with an arrow).

Example 7

Detection of Gastric Cancer by Measurement of Human Cofilin 1 Protein in Blood Plasma The human cofilin 1 protein in blood plasma samples from gastric cancer patients and healthy subjects were detected by the sandwich ELISA method using biotin-labeled 1E2 and biotin-labeled 4E12. Blood was collected from 51 gastric cancer patients (stage I: 24 patients, stage II: 6 patients, stage III: 11 patients, stage 1V: 10 patients) and 20 control healthy subjects using a Benedict II blood vacuuming tube (Terumo Corporation), thereby obtaining blood plasma samples. Each blood plasma sample was diluted 10-fold with TBS buffer containing 1% BSA and 1% NP40, and then 100 μA thereof was used as a sample.

Figure 5:
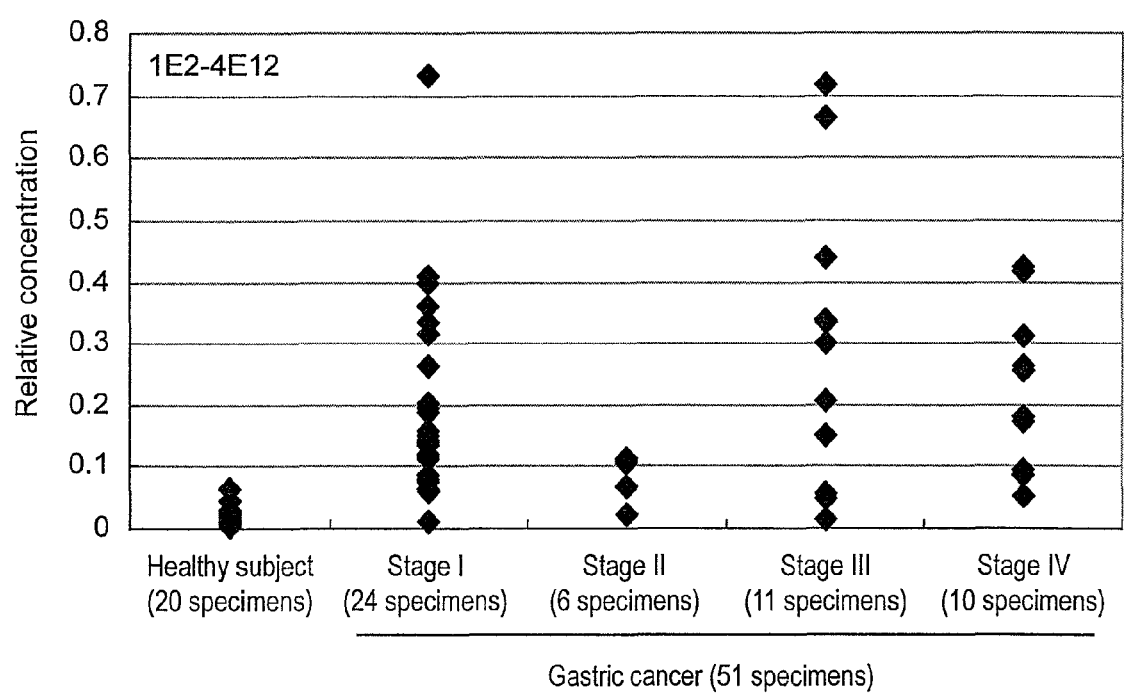
FIG. 5 is a graph showing the results of detecting the cofilin 1 protein in blood plasma of gastric cancer patients and healthy subjects by sandwich ELISA.

First, a 3 μg/mL solution of 1E2 anti-human cofilin 1 antibody was prepared, and then 100 μL each of the solution was added to each well of a flat bottom 96-well plate (Nunc), followed by 5 hours of immobilization. The purified antibody solution within each well was discarded, 400 μL of a blocking solution (PBS-T containing 1% BSA) was poured thereinto, and then the plate was left to stand overnight at 4° C. The blocking solution was removed, the plate was washed once with 400 μl of PBS-T, and then 100 μl of a blood plasma sample was added, followed by 1 hour of reaction at room temperature. The solution within each well was discarded, the plate was washed with PBS-T, and then biotin-labeled 4E12 diluted with TBS buffer containing 1% NP40 to 0.5 μg/mL was added at 100 μA per well, followed by 1 hour of reaction at room temperature. Subsequently, the solution within each well was discarded, the plate was washed with PBS-T, and then 100 μL of an avidin-HRP solution (R&D) underwent reaction for 1 hour at room temperature. Thereafter, the avidin-HRP solution was discarded, the plate was washed with PBS-T, and then 100 μL of the TMB solution was added for 5 minutes of reaction. The reaction was stopped by adding 100 μL of a 2N sulfuric acid solution. Color development was confirmed by measuring absorbance at 450 nm. As a result, the human cofilin 1 protein was detected at statistically significantly higher levels in the blood plasma samples from early and advanced gastric cancer patients than blood plasma samples from control healthy subjects (FIG. 5).

Example 8

Detection of Gastric Cancer by Measurement of Human Cofilin 1 Protein in Serum

The human cofilin 1 in sera of gastric cancer patients and healthy subjects were detected by the sandwich ELISA method using biotin-labeled 1E2 and biotin-labeled 4E12. Blood was collected from 15 gastric cancer patients (stage I: 7 patients; stage II: 1 patient; stage III: 4 patients; stage IV: 3 patients) and 5 control healthy subjects using a Benedict II blood vacuuming tube (Terumo Corporation), so as to obtain sera. Each serum sample was diluted 10-fold with TBS buffer containing 1% BSA and 1% NP40, and then 100 μL of each solution was used as a sample.

Figure 6:
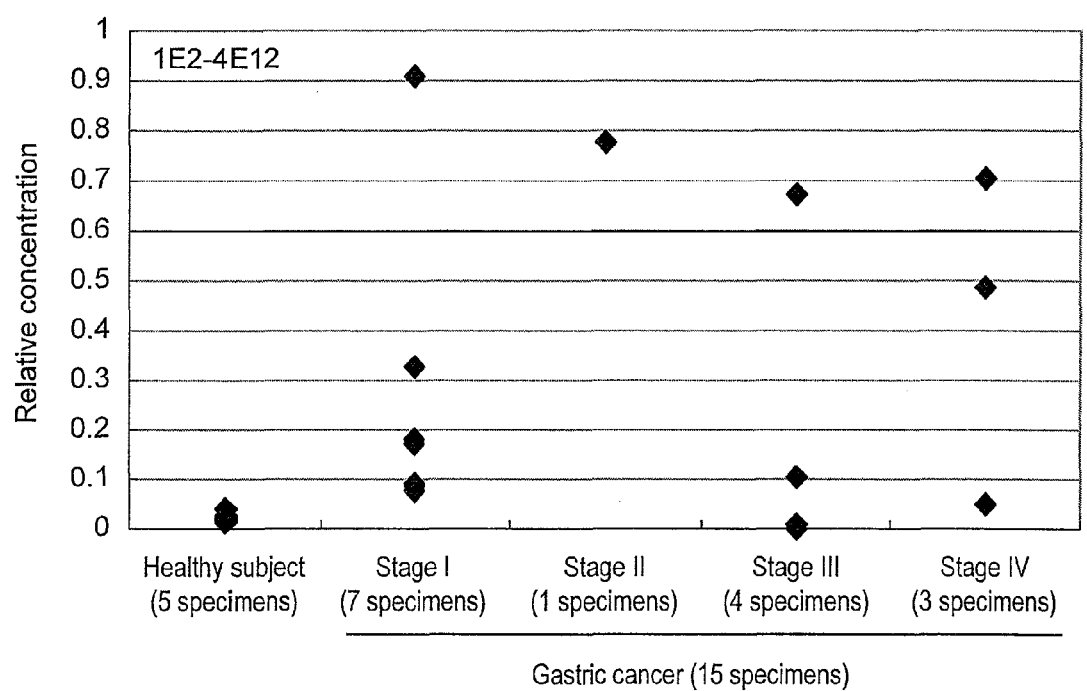
FIG. 6 is a graph showing the results of detecting the cofilin 1 protein in sera of gastric cancer patients and healthy subjects by sandwich ELISA.

First, a 3 μg/mL solution of 1E2 anti-human cofilin 1 antibody was prepared. 100 μl, each of the solution was added to each well of a flat bottom 96-well plate (Nunc), followed by 5 hours of immobilization. The purified antibody solution within each well was discarded, 400 μl of a blocking solution (PBS-T containing 1% BSA) was poured thereinto, and then the plate was left to stand overnight at 4° C. The blocking solution was removed, the plate was washed once with 400 μL of PBS-T, and then 100 μL of a serum sample was added, followed by 1 hour of reaction at room temperature. The solution within each well was discarded, the plate was washed with PBS-T, and then biotin-labeled 4E12 diluted with TBS buffer containing 1% NP40 to 0.5 μg/mL was added at 100 μL per well, followed by 1 hour of reaction at room temperature. Subsequently, the solution within each well was discarded, the plate was washed with PBS-T, and then 100 μL of an avidin-HRP solution (R&D) underwent reaction for 1 hour at room temperature. Thereafter, the avidin-HRP solution was discarded, the plate was washed with PBS-T, and 100 μl of the TMB solution was added for 5 minutes of reaction. The reaction was stopped by adding 100 μL of a 2N sulfuric acid solution. Color development was confirmed by measuring absorbance at 450 nm. As a result, the human cofilin 1 protein was detected at statistically significantly higher levels in serum samples from early and advanced gastric cancer patients than serum samples from control healthy subjects (FIG. 6).

INDUSTRIAL APPLICABILITY

The present invention enables to quantitatively detect with high sensitivity the cofilin 1 protein that is present in biological samples derived from various mammalian cells. Furthermore, according to the method of the present invention, early gastrointestinal cancer can be detected with high sensitivity using patients' blood. Hence, the method of the present invention is also useful as a method for screening for an early cancer patient using a noninvasive testing technique. Moreover, the method of the present invention is also useful as an assay system to be used in basic research for the purpose of elucidating a cytoskeleton regulatory mechanism in which the cofilin 1 protein is involved.

All publications, patents, and patent applications cited herein are incorporated herein by reference in their entirety.

The invention claimed is:

1. An anti-cofilin 1 monoclonal antibody or a fragment thereof, which specifically recognizes an epitope that is present in
a peptide region comprising at least the amino acid sequence shown in SEQ ID NO: 5 in the amino acid sequence shown in SEQ ID NO: 1.

2. The anti-cofilin 1 monoclonal antibody or a fragment thereof according to claim 1, wherein
in the light chain, CDR1 comprises the sequence shown in SEQ ID NO: 8, CDR2 comprises the sequence shown in SEQ ID NO: 9, and CDR3 comprises the sequence shown in SEQ ID NO: 10, and
in the heavy chain, CDR1 comprises the sequence shown in SEQ ID NO: 11, CDR2 comprises the sequence shown in SEQ ID NO: 12, and CDR3 comprises the sequence shown in SEQ ID NO: 13.

3. The anti-cofilin 1 monoclonal antibody or a fragment thereof according to claim 1, wherein
in the light chain, CDR1 comprises the sequence shown in SEQ ID NO: 14, CDR2 comprises the sequence shown in SEQ ID NO: 15, and CDR3 comprises the sequence shown in SEQ ID NO: 16, and
in the heavy chain, CDR1 comprises the sequence shown in SEQ ID NO: 17, CDR2 comprises the sequence shown in SEQ ID NO: 18, and CDR3 comprises the sequence shown in SEQ ID NO: 19.

4. An anti-cofilin 1 monoclonal antibody or a fragment thereof, which specifically recognizes an epitope that is present in
a peptide region comprising at least the amino acid sequence shown in SEQ ID NO: 6 in the amino acid sequence shown in SEQ ID NO: 1.

5. The anti-cofilin 1 monoclonal antibody or a fragment thereof according to claim 4, wherein
in the light chain, CDR1 comprises the sequence shown in SEQ ID NO: 20, CDR2 comprises the sequence shown in SEQ ID NO: 21, and CDR3 comprises the sequence shown in SEQ ID NO: 22, and
in the heavy chain, CDR1 comprises the sequence shown in SEQ ID NO: 23, CDR2 comprises the sequence shown in SEQ ID NO: 24, and CDR3 comprises the sequence shown in SEQ ID NO: 25.

6. An anti-cofilin 1 monoclonal antibody or a fragment thereof, which specifically recognizes an epitope that is present in
a peptide region comprising at least the amino acid sequence shown in SEQ ID NO: 7 in the amino acid sequence shown in SEQ ID NO: 2.

7. The anti-cofilin 1 monoclonal antibody or a fragment thereof according to claim 6, wherein
in the light chain, CDR1 comprises the sequence shown in SEQ ID NO: 26, CDR2 comprises the sequence shown in SEQ ID NO: 27, and CDR3 comprises the sequence shown in SEQ ID NO: 28, and
in the heavy chain, CDR1 comprises the sequence shown in SEQ ID NO: 29, CDR2 comprises the sequence shown in SEQ ID NO: 30, and CDR3 comprises the sequence shown in SEQ ID NO: 31.

8. An immunoassay of cofilin 1 protein, comprising measuring cofilin 1 and/or a fragment thereof in a sample using two or more types of anti-cofilin 1 monoclonal antibodies and/or fragments thereof that specifically recognize different epitopes on the amino acid sequence of the cofilin 1 protein,
wherein the different epitopes are present in the peptide regions consisting of the amino acid sequences shown in SEQ ID NO: 1 and/or 2.

9. The immunoassay according to claim 8, wherein the different epitopes are present in a peptide region comprising at least the amino acid sequence shown in SEQ ID NO: 3 in the peptide region consisting of the amino acid sequence shown in SEQ ID NO: 1, and/or a peptide region comprising at least the amino acid sequence shown in SEQ ID NO: 4 in the peptide region consisting of the amino acid sequence shown in SEQ ID NO: 2.

10. The immunoassay according to claim 8, wherein the different epitopes are present in the peptide regions comprising at least the amino acid sequences shown in SEQ ID NO: 5 and/or 6 in the peptide region consisting of the amino acid sequence shown in SEQ ID NO: 1, and/or a peptide region comprising at least the amino acid sequence shown in SEQ ID NO: 7 in the peptide region consisting of the amino acid sequence shown in SEQ ID NO: 2.

11. An immunoassay of cofilin 1 protein, comprising measuring cofilin 1 and/or a fragment thereof in a sample using two or more types of anti-cofilin 1 monoclonal antibodies and/or fragments thereof that specifically recognize different epitopes on the amino acid sequence of the cofilin 1 protein,
wherein the different epitopes are separately present in two peptide regions selected from the peptide regions consisting of the amino acid sequences shown in SEQ ID NOS: 5 to 7.

12. The immunoassay according to claim 8, wherein the different epitopes are present in a peptide region consisting of 6 or more and 21 or less continuous amino acids in the peptide regions consisting of the amino acid sequences shown in SEQ ID NO: 1 and/or 2.

13. The immunoassay according to claim 8, wherein the above 2or more types of anti-cofilin 1 monoclonal antibodies and/or fragments thereof are selected from the anti-cofilin 1 monoclonal antibodies or fragments thereof including:
(1) a first type of anti-cofilin 1 monoclonal antibody or a fragment thereof, which specifically recognizes an epitope that is present in
a peptide region comprising at least the amino acid sequence shown in SEQ ID NO: 5 in the amino acid sequence shown in SEQ ID NO: 1,
wherein
in the light chain, CDR1 comprises the sequence shown in SEQ ID NO: 8, CDR2comprises the sequence shown in SEQ ID NO: 9, and CDR3 comprises the sequence shown in SEQ ID NO: 10, and
in the heavy chain, CDR1 comprises the sequence shown in SEQ ID NO: 11, CDR2 comprises the sequence shown in SEQ ID NO: 12, and CDR3 comprises the sequence shown in SEQ ID NO: 13;
(2) a second type of anti-cofilin 1 monoclonal antibody or a fragment thereof, which specifically recognizes an epitope that is present in
a peptide region comprising at least the amino acid sequence shown in SEQ ID NO: 5 in the amino acid sequence shown in SEQ ID NO: 1,
wherein
in the light chain, CDR1 comprises the sequence shown in SEQ ID NO: 14, CDR2 comprises the sequence shown in SEQ ID NO: 15, and CDR3 comprises the sequence shown in SEQ ID NO: 16, and
in the heavy chain, CDR1 comprises the sequence shown in SEQ ID NO: 17, CDR2 comprises the sequence shown in SEQ ID NO: 18, and CDR3 comprises the sequence shown in SEQ ID NO: 19;
(3) a third type of anti-cofilin 1 monoclonal antibody or a fragment thereof, which specifically recognizes an epitope that is present in a peptide region comprising at least the amino acid sequence shown in SEQ ID NO: 6 in the amino acid sequence shown in SEQ ID NO: 1 wherein in the light chain, CDR1 comprises the sequence shown in SEQ ID NO: 20, CDR2 comprises the sequence shown in SEQ ID NO: 21, and CDR3 comprises the sequence shown in SEQ ID NO: 22, and in the heavy chain, CDR1 comprises the sequence shown in SEQ ID NO: 23, CDR2 comprises the sequence shown in SEQ ID NO: 24, and CDR3 comprises the sequence shown in SEQ ID NO: 25; and (4) a fourth type of anti-cofilin 1 monoclonal antibody or a fragment thereof, which specifically recognizes an epitope that is present in a peptide region comprising at least the amino acid sequence shown in SEQ ID NO: 7 in the amino acid sequence shown in SEQ ID NO: 2, wherein in the light chain, CDR1 comprises the sequence shown in SEQ ID NO: 26, CDR2 comprises the sequence shown in SEQ ID NO: 27, and CDR3 comprises the sequence shown in SEQ ID NO: 28, and in the heavy chain, CDR1 comprises the sequence shown in SEQ ID NO: 29, CDR2 comprises the sequence shown in SEQ ID NO: 30, and CDR3 comprises the sequence shown in SEQ ID NO: 31.

14. The immunoassay according to claim 13, wherein the 2 types of anti-cofilin 1 monoclonal antibody and/or fragments thereof constitute anyone of the following combinations of anti-cofilin 1 monoclonal antibodies and/or fragments thereof:

a) a combination of first and third types of anti-cofilin 1 monoclonal antibodies and/or the fragments thereof, said first type being a type that specifically recognizes an epitope that is present in a peptide region comprising at least the amino acid sequence shown in SEQ ID NO: 5 in the amino acid sequence shown in SEQ ID NO: 1, wherein in the light chain, CDR1 comprises the sequence shown in SEQ ID NO: 8, CDR2 comprises the sequence shown in SEQ ID NO: 9, and CDR3 comprises the sequence shown in SEQ ID NO: 10, and in the heavy chain, CDR1 comprises the sequence shown in SEQ ID NO: 11, CDR2 comprises the sequence shown in SEQ ID NO: 12, and CDR3 comprises the sequence shown in SEQ ID NO: 13; and said third type being a type that specifically recognizes an epitope that is present in a peptide region comprising at least the amino acid sequence shown in SEQ ID NO: 6 in the amino acid sequence shown in SEQ ID NO: 1 wherein in the light chain, CDR1 comprises the sequence shown in SEQ ID NO: 20, CDR2 comprises the sequence shown in SEQ ID NO: 21, and CDR3 comprises the sequence shown in SEQ ID NO: 22, and in the heavy chain, CDR1 comprises the sequence shown in SEQ ID NO: 23, CDR2 comprises the sequence shown in SEQ ID NO: 24, and CDR3 comprises the sequence shown in SEQ ID NO: 25;

b) a combination of first and fourth types of anti-cofilin 1 monoclonal antibodies and/or fragments thereof with said first type being recited above, and said fourth type being a type that specifically recognizes an epitope that is present in a peptide region comprising at least the amino acid sequence shown in SEQ ID NO: 7 in the amino acid sequence shown in SEQ ID NO: 2, wherein in the light chain, CDR1 comprises the sequence shown in SEQ ID NO: 26, CDR2 comprises the sequence shown in SEQ ID NO: 27, and CDR3 comprises the sequence shown in SEQ ID NO: 28, and in the heavy chain, CDR1 comprises the sequence shown in SEQ ID NO: 29, CDR2 comprises the sequence shown in SEQ ID NO: 30, and CDR3 comprises the sequence shown in SEQ ID NO: 31;

c) a combination of second and fourth types of anti-cofilin 1 monoclonal antibodies and/or fragments thereof with said fourth type being recited above and said second type being a type that specifically recognizes an epitope that is present in a peptide region comprising at least the amino acid sequence shown in SEQ ID NO: 5 in the amino acid sequence shown in SEQ ID NO: 1, wherein in the light chain, CDR1 comprises the sequence shown in SEQ ID NO: 14, CDR2 comprises the sequence shown in SEQ ID NO: 15, and CDR3 comprises the sequence shown in SEQ ID NO: 16, and in the heavy chain, CDR1 comprises the sequence shown in SEQ ID NO: 17, CDR2 comprises the sequence shown in SEQ ID NO: 18, and CDR3 comprises the sequence shown in SEQ ID NO: 19; and d) a combination of third and fourth type anti-cofilin 1 monoclonal antibodies and/or fragments thereof with said third and fourth types being recited above.

15. The immunoassay according to claim 8, wherein the sample is blood, urine, cell supernatant, cell extract, tissue extract, gastric juice, saliva, lymph fluid, lacrimal fluid, or seminal fluid.

16. A kit for cofilin 1 protein quantification, containing two or more types of anti-cofilin 1 monoclonal antibodies and/or fragments thereof, which specifically recognize different epitopes of the cofilin 1 protein, wherein the two or more types of anti-cofilin 1 monoclonal antibodies and/or fragments thereof are selected from the group consisting of:

(A) a type of anti-cofilin 1 monoclonal antibody or a fragment thereof, which specifically recognizes an epitope that is present in a peptide region comprising at least the amino acid sequence shown in SEQ ID NO: 5 in the amino acid sequence shown in SEQ ID NO: 1

(B) a type of anti-cofilin 1 monoclonal antibody or a fragment thereof having the properties and regions of said type (A), wherein in the light chain, CDR1 comprises the sequence shown in SEQ ID NO: 8, CDR2comprises the sequence shown in SEQ ID NO: 9, and CDR3 comprises the sequence shown in SEQ ID NO: 10, and in the heavy chain, CDR1 comprises the sequence shown in SEQ ID NO: 11, CDR2 comprises the sequence shown in SEQ ID NO: 12, and CDR3 comprises the sequence shown in SEQ ID NO: 13;

(C) a type of anti-cofilin 1 monoclonal antibody or a fragment thereof, which specifically recognizes an epitope that is present in a peptide region comprising at least the amino acid sequence shown in SEQ ID NO: 5 in the amino acid sequence shown in SEQ ID NO: 1;

(D) a type of anti-cofilin 1 monoclonal antibody or a fragment thereof having the properties and regions of said type (C), wherein in the light chain, CDR1 comprises the sequence shown in SEQ ID NO: 14, CDR2 comprises the sequence shown in SEQ ID NO: 15, and CDR3 comprises the sequence shown in SEQ ID NO: 16, and in the heavy chain, CDR1 comprises the sequence shown in SEQ ID NO: 17, CDR2 comprises the sequence shown in SEQ ID NO: 18, and CDR3 comprises the sequence shown in SEQ ID NO: 19;

(E) a type of anti-cofilin 1 monoclonal antibody or a fragment thereof, which specifically recognizes an epitope that is present in a peptide region comprising at least the amino acid sequence shown in SEQ ID NO: 6 in the amino acid sequence shown in SEQ ID NO: 1;

(F) a type of anti-cofilin 1 monoclonal antibody or a fragment thereof having the properties and regions of said type (E), wherein in the light chain, CDR1 comprises the sequence shown in SEQ ID NO: 20, CDR2 comprises the sequence shown in SEQ ID NO: 21, and CDR3 comprises the sequence shown in SEQ ID NO: 22, and in the heavy chain, CDR1 comprises the sequence shown in SEQ ID NO: 23, CDR2 comprises the sequence shown in SEQ ID NO: 24, and CDR3 comprises the sequence shown in SEQ ID NO: 25;

(G) a type of anti-cofilin 1 monoclonal antibody or a fragment thereof, which specifically recognizes an epitope that is present in a peptide region comprising at least the amino acid sequence shown in SEQ ID NO: 7 in the amino acid sequence shown in SEQ ID NO: 2; and (H) a type of anti-cofilin 1 monoclonal antibody or a fragment thereof having the properties and regions of said type (G), wherein in the light chain, CDR1 comprises the sequence shown in SEQ ID NO: 26, CDR2 comprises the sequence shown in SEQ ID NO: 27, and CDR3 comprises the sequence shown in SEQ ID NO: 28, and in the heavy chain, CDR1 comprises the sequence shown in SEQ ID NO: 29, CDR2 comprises the sequence shown in SEQ ID NO: 30, and CDR3 comprises the sequence shown in SEQ ID NO: 31.

17. The immunoassay according to claim 11, wherein the sample is blood, urine, cell supernatant, cell extract, tissue extract, gastric juice, saliva, lymph fluid, lacrimal fluid, or seminal fluid.

* * * * *